United States Patent
Huang et al.

(10) Patent No.: US 12,257,268 B2
(45) Date of Patent: *Mar. 25, 2025

(54) ANTITUMOR APPLICATION OF POLYSACCHARIDE CARBON NANOGELS

(71) Applicant: National Taiwan Ocean University, Keelung (TW)

(72) Inventors: Chih-Ching Huang, Keelung (TW); Ju-Yi Mao, Kaohsiung (TW); Chen-Yow Wang, Yunlin County (TW)

(73) Assignee: NATIONAL TAIWAN OCEAN UNIVERSITY, Keelung (TW)

( * ) Notice: Subject to any disclaimer, the term of this patent is extended or adjusted under 35 U.S.C. 154(b) by 584 days.

This patent is subject to a terminal disclaimer.

(21) Appl. No.: 17/666,538

(22) Filed: Feb. 7, 2022

(65) Prior Publication Data

US 2022/0257638 A1    Aug. 18, 2022

Related U.S. Application Data

(63) Continuation-in-part of application No. 17/169,637, filed on Feb. 8, 2021, now Pat. No. 11,672,819.

(51) Int. Cl.
| | |
|---|---|
| *A61K 31/734* | (2006.01) |
| *A61K 9/06* | (2006.01) |
| *A61K 47/02* | (2006.01) |
| *B82Y 5/00* | (2011.01) |
| *B82Y 30/00* | (2011.01) |

(52) U.S. Cl.
CPC ............ *A61K 31/734* (2013.01); *A61K 9/06* (2013.01); *A61K 47/02* (2013.01); *B82Y 5/00* (2013.01); *B82Y 30/00* (2013.01)

(58) Field of Classification Search
CPC ... A61K 8/21; A61K 8/24; A61K 8/41; A61K 2800/28; A61K 31/734; A61K 9/06; A61K 47/02; A61Q 11/00; B82Y 5/00; B82Y 30/00
See application file for complete search history.

(56) References Cited

U.S. PATENT DOCUMENTS

| 9,233,166 B2 * | 1/2016 | Dai ............... A61K 47/6949 |
| 11,672,819 B2 * | 6/2023 | Mao ............... A61K 9/5161 |
| | | 424/488 |

OTHER PUBLICATIONS

M. Wang et al. "Transformation of lignosulfonate into graphene-like 2D nanosheets: Self-assembly mechanism and their potential in biomedical and electrical applications," International Journal of Biological Macromolecules 128 (2019) 621- 628. (Year: 2019).*
Fan L. et al., Sodium alginate conjugated graphene oxide as a new carrier for drug delivery system, Int. J. Biol. Macromol., Sep. 9, 2016, pp. 582-590, v.93, Elsevier, Amsterdam, Netherlands.
Zhao W. et al., Morphology and Thermal Properties of Calcium Alginate/Reduced Graphene Oxide Composites, Polymers, Sep. 5, 2018, p. 990, v.10(9), MDPI, Basel, Switzerland.
Venkatesan J. et al., Seaweed Polysaccharide-Based Nanoparticles: Preparation and Applications for Drug Delivery, Polymers, Jan. 26, 2016, p. 30, v.8(2), MDPI, Basel, Switzerland.
Debrle T. A. et al., Polysaccharide based nanogels in the drug delivery system: Application as the carrier of pharmaceutical agents, Mater. Sci. Eng. A., Nov. 1, 2016, pp. 964-981, v.68, Elsevier, Amsterdam, Netherlands.

* cited by examiner

*Primary Examiner* — Michael P Cohen
(74) *Attorney, Agent, or Firm* — Chun-Ming Shih; LANWAY IPR SERVICES

(57) ABSTRACT

The present invention provides a polysaccharide carbon nanogel exhibiting antitumor efficacy prepared by carbonizing the polysaccharide utilizing dry heating. The polysaccharide carbon nanogel comprises a graphene-like nanosheet and a polysaccharide, which are complexed to form a cross-linked supramolecular structure. The polysaccharide carbon nanogels has an exceptional polyphenolic structure and high antimetastatic activity, which can become a promising anti-tumor drug.

18 Claims, 38 Drawing Sheets

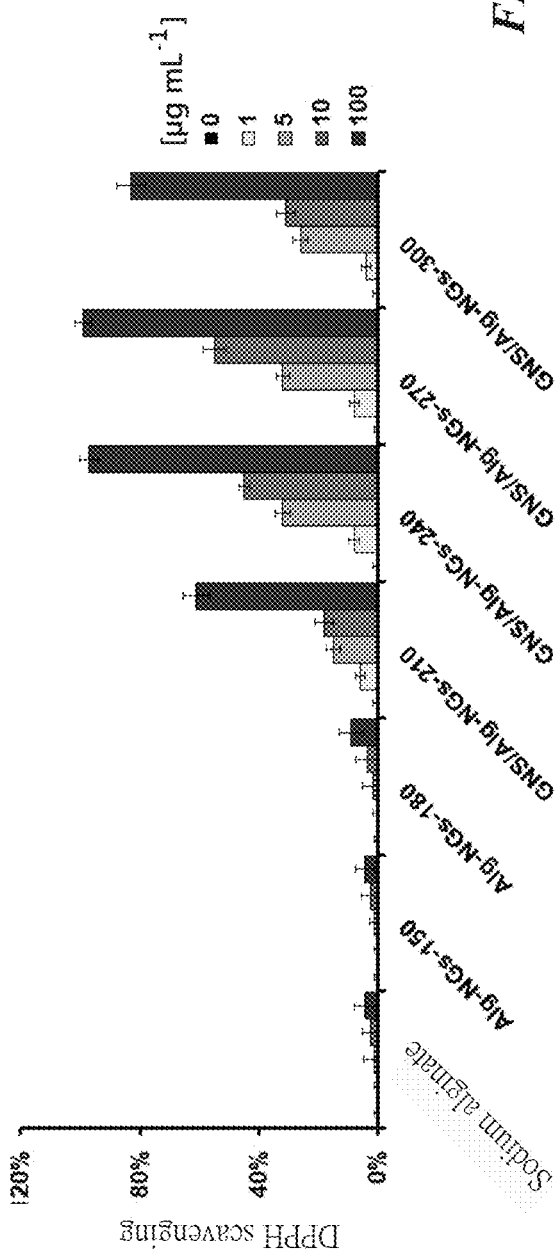
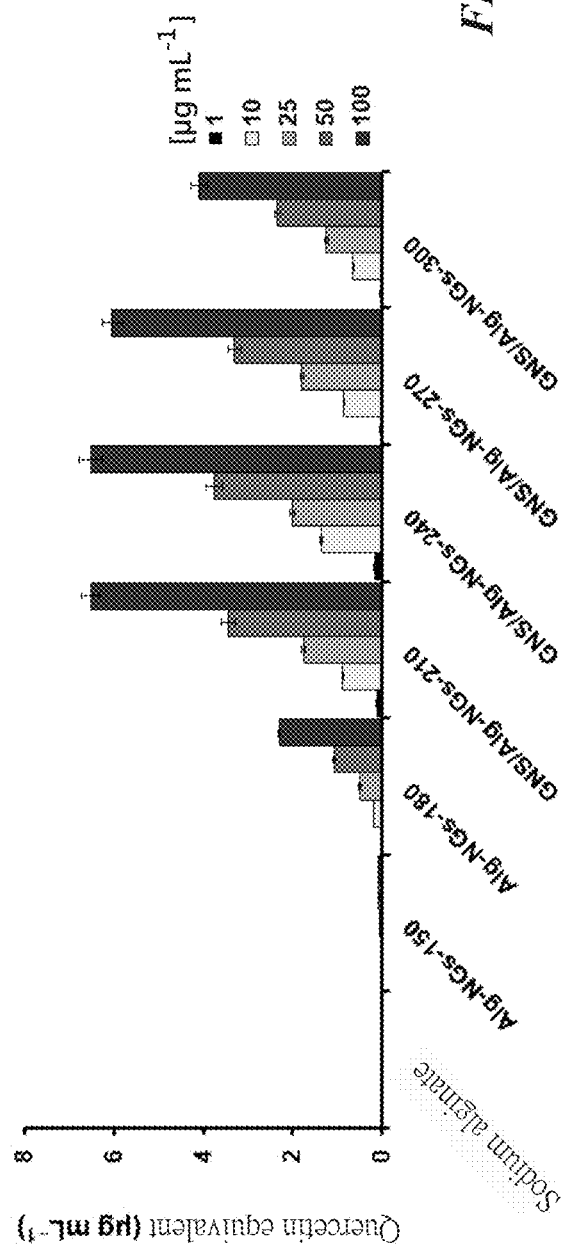
FIG. 14A
FIG. 14B

ANTITUMOR APPLICATION OF POLYSACCHARIDE CARBON NANOGELS

CROSSED-REFERENCE TO RELATED APPLICATION

This application claims priority to and the benefit of U.S. patent application Ser. No. 17/169,637, filed on Feb. 8, 2021, in the United States Patent and Trademark Office, the entire content of which is incorporated herein by reference.

BACKGROUND OF THE INVENTION

1. Field of the Invention

The present disclosure relates to the field of nanopolymer engineering. More particularly, the present disclosure relates to phenolic-polysaccharide nanogels and the use thereof for antitumor applications.

2. Description of the Prior Art

Despite rapid advances in medicine, cancer continues to be the top three leading cause of death in the world. Most of the current drugs for the treatment of cancer are mainly chemically synthesized drugs, such as doxorubicin. However, chemical drugs have no target characteristics, and normal cells are still killed at the same time, causing excessive side effects. In addition, the biologically active molecules of chemical drugs are easily decomposed by organisms, and multiple injections are required to maintain the drug efficacy. In addition, chemotherapy can easily lead to the generation of drug-resistant tumor cells, which often limits the efficacy of chemotherapy in cancer treatment and the survival rate of patients.

Especially when cancer cells metastasize from the primary tumor to other organs or parts of the body to form secondary tumors, the prognosis is usually not very optimistic, and the mortality rate is also greatly increased. Therefore, tumor metastasis (metastasis of cancer cells) is regarded as the cancer's ace in the hole. As long as it is generally understood that tumor metastasis is through the attachment of proliferating cancer cells to epidermal cells, the cancer cells crawl to the outer surface of blood vessels via cell migration, and then invade the blood vessel wall, transfer to other parts of the body along the blood vessels, and then invade cells at metastatic sites from the inner wall of blood vessels. Therefore, the development of drugs that can slow or inhibit tumor metastasis is also the focus of current cancer research Natural polyphenol molecules that consist of multiples of phenol structural units are widely distributed in fruits, vegetables, seeds, and various species of algae. They possess anticancer, antidiabetic, anti-inflammatory, antioxidant, and anticoagulation functionalities (*Molecules* 2016; 21: 708; *Crit. Rev. Food Sci. Nutr.* 2016; 56: 419-444; *Nutrients* 2016; 8: 552). However, natural polyphenolic acid compounds suffer from stability issues and their low abundance, and complex extraction and purification processes are too expensive to apply in cancer treatment and determine their efficacy. Therefore, it is still necessary to further develop materials that are more stable, can be widely used in the human body, and can have therapeutic effects on cancer.

SUMMARY OF THE INVENTION

In view of the foregoing, the present disclosure provides a bioinspired and eco-friendly approach for the one-pot synthesis of nanogels from cost-effective and easily available polysaccharides without needing to employ any catalyst and hazardous solvents.

In one aspect, the present disclosure provides a use of a nanogel in the preparation of pharmaceutical composition for treating tumor disease or neoplastic disorder, wherein the nanogel comprising a graphene-like nanosheet and a polysaccharide, and wherein the graphene-like nanosheet comprises a carbonization product of at least a portion of the polysaccharide and the graphene-like nanosheet is complexed with the polysaccharide to form a cross-linked supramolecular structure.

In some embodiments, the carbonization product is formed by dry heating the polysaccharide to be carbonized.

In at least one embodiment, the polysaccharide is a salt of alginic acid, such as sodium alginate, calcium alginate, magnesium alginate, and any combination thereof.

In at least one embodiment, the polysaccharide has a free end and a fixed end, and the fixed end of the polysaccharide is bonded to the surface of the graphene-like nanosheet.

In at least one embodiment, the cross-linked supramolecular structure has a functional group on the surface thereof. In some embodiments, the functional group is selected from the group consisting of hydroxyl, ester, phenol, carboxyl and any combination thereof.

In at least one embodiment, the phenolic-polysaccharide nanogel has a hydrodynamic diameter ranging from 20 nm to 490 nm, e.g., a hydrodynamic diameter with a lower limit not less than 20 nm or with an upper limit not greater than 490 nm. In some embodiments, the phenolic-polysaccharide nanogel has a hydrodynamic diameter ranging from 40 nm to 450 nm, e.g., about 45 nm, about 50 nm, about 60 nm, about 80 nm, about 100 nm, about 120 nm, about 150 nm, about 180 nm, about 200 nm, about 225 nm, about 250 nm, about 275 nm, about 300 nm, about 350 nm, about 400 nm, about 425 nm, about 450 nm and about 460 nm.

In at least one embodiment, the phenolic-polysaccharide nanogel has a zeta (ζ) potential ranging from −26.5 mV to −47.5 mV, e.g., a zeta potential with a lower limit not less than −47.5 mV or with an upper limit not greater than −26.5 mV. In some embodiments, the phenolic-polysaccharide nanogel has a zeta potential ranging from −30 mV to −45 mV, e.g., about −32.5 mV, about −35 mV, about −37.5 mV, about −40 mV, and about −42.5 mV.

In at least one embodiment, the graphene-like nanosheet has lattice planes of the (100) and (112) facets.

In one aspect, the present disclosure also provides a method of preparing the above phenolic-polysaccharide nanogels, comprising carbonizing the polysaccharide by dry heating.

In at least one embodiment, the dry heating is performed at a temperature ranging from 150° C. to 300° C., e.g., a temperature with a lower limit not less than 150° C. or with an upper limit not greater than 300° C. In some embodiments, the heating temperature ranges from 180° C. to 300° C., e.g., about 190° C., about 200° C., about 210° C., about 220° C., about 230° C., about 240° C., about 250° C., about 260° C., about 270° C., about 280° C. and about 290° C.

In another aspect, the present disclosure provides a use of any one of the above phenolic-polysaccharide nanogels for treating tumor disease or neoplastic disorder.

In another aspect, the present disclosure provides a use of any one of the above phenolic-polysaccharide nanogels for preventing or treating metastasis.

In another aspect, the present disclosure provides a pharmaceutical composition for treating tumor disease or neoplastic disorder. The pharmaceutical composition comprises any one of the above phenolic-polysaccharide nanogels and a pharmaceutically acceptable vehicle thereof.

In a further aspect, the present disclosure provides a pharmaceutical composition for preventing or treating metastasis. The composition comprises any one of the above phenolic-polysaccharide nanogel and a pharmaceutically acceptable vehicle thereof.

In a yet further aspect, the present disclosure provides a method for preventing or treating metastasis in a subject in need thereof, comprising administering to the subject any one of the above pharmaceutical compositions.

In at least one embodiment, the tumor disease or neoplastic disorder may be selected from the group consisting of DPPH, bone cancer, blood cancer, breast cancer, melanoma, thyroid cancer, parathyroid cancer, bone marrow cancer, rectal cancer, throat cancer, laryngeal cancer, lung cancer, esophagus cancer, pancreatic cancer, stomach cancer, tongue cancer, skin cancer, brain tumor, uterine cancer, head and neck cancer, gallbladder cancer, oral cancer, colon cancer, anal and perianal cancers, central nervous system tumors, liver cancer, and colorectal cancer.

The nanogels provided in the present disclosure are graphene-like nanosheet-embedded polyphenolic-alginate nanogels (hereinafter referred to as "GNS/Alg-NGs"), which are formed through polycondensation (cross-linking), carbonization, and in situ passivation during the dry heating of polysaccharide (e.g., sodium alginate) without utilizing any chemical catalyst or solvent. In addition, the graphene-like embedded quantum dots (GQDs) alginate nanogel (GNS/Alg-NGs) has functional group like polyphenolic acid, thus possessing good antioxidant activity. GNS/Alg-NGs display high aqueous solubility, biocompatibility, these features can reduce side effects in treatment. The resistance of cancer cell migration experiments, inhibition of cancer cell invasion experiments and animal experiments show excellent anti-tumor metastasis activity and tumor tissue retention. It has a high potential for synergistic therapy with current cancer drugs, and can also become a potential treatment for cancer.

BRIEF DESCRIPTION OF THE DRAWINGS

The present disclosure can be more fully understood by reading the following descriptions of the embodiments, with reference made to the accompanying drawings.

FIG. 11A shows the constant TGA data of sodium alginate at 150° C. to 300° C. 150: Alg-NGs-150; 180: Alg-NGs-180; 210: GNS/Alg-NGs-210; 240: GNS/Alg-NGs-240; 270: GNS/Alg-NGs-270; 300: GNS/Alg-NGs-300. FIG. 11B shows the temperature-dependent TGA of sodium alginate. FIG. 11C shows the DSC curve of sodium alginate.

FIGS. 14A and 14B show the comparison of antioxidant activity of sodium alginate, Alg-NGs-150, Alg-NGs-180, GNS/Alg-NGs-210, GNS/Alg-NGs-240, GNS/Alg-NGs-270 and GNS/Alg-NGs-300 by DPPH scavenging assay and Folin-Ciocalteu assay, respectively.

FIG. 18A (b) sequentially shows the experiment result pictures of inhibition effect of control group, GNS/Alg-NGs-270 at 10 μg/mL, 50 μg/mL, 100 μg/mL, and 400 μg/mL on cancer cell invasion. FIG.

18B (a) shows scale bars of cell migration rate in the groups of FIG. 18A (a) (*p<0.05, ***p<0.001, n=3).

DETAILED DESCRIPTION OF THE PREFERRED EMBODIMENT

Figure 1:
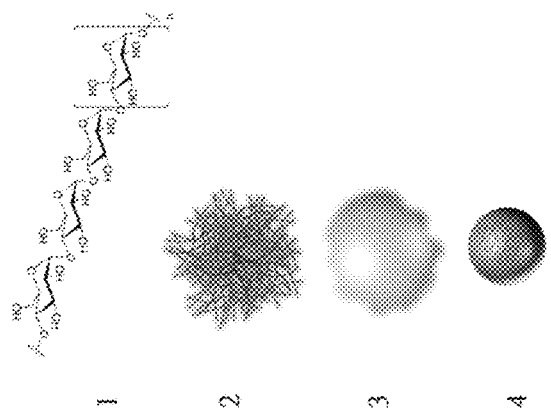
FIG. 1 shows schematic diagrams illustrating the preparation of GNS/Alg-NGs and the estimated structure of Carbon Quantum Dots (CQD) of GNS/Alg-NG, wherein 1 represents the structural formula of alginate, 2 represents the polymer with partial carbonization, 3 represents the nanogel, and 4 represents the graphite.
Figure 1:
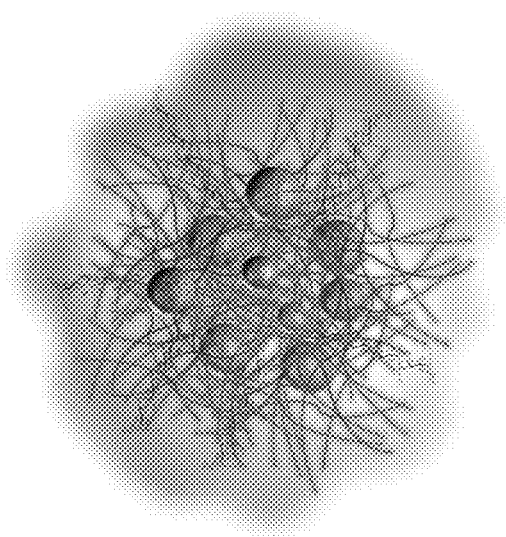
Figure 1:
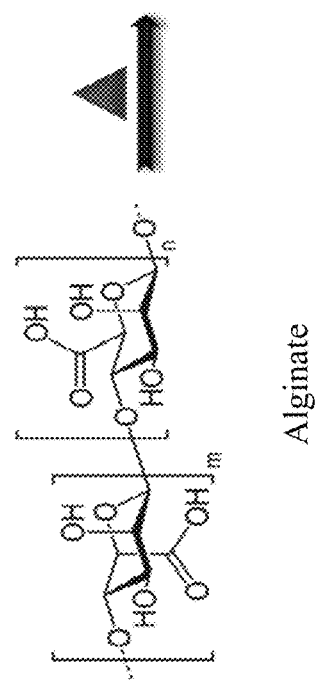

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the following examples for carrying out this disclosure without contravening its scope, for different aspects and applications.

It is further noted that, as used in this disclosure, the singular forms "a," "an," and "the" include plural referents, unless expressly and unequivocally limited to one referent. The term "or" is used interchangeably with the term "and/or," unless the context clearly indicates otherwise.

As used herein, the term "comprising" or "comprises" is used in reference to compositions, methods, and respective component(s) thereof, which are included in the present disclosure, yet open to the inclusion of unspecified elements.

The present disclosure is directed to a phenolic-polysaccharide nanogel useful for treating cancer. The phenolic-polysaccharide nanogel comprises a graphene-like nanosheet and a polysaccharide, wherein the graphene-like nanosheet comprises a carbonization product of at least a portion of the polysaccharide, and is complexed with the polysaccharide to form a cross-linked supramolecular structure. In some embodiments, the polysaccharide used for the preparation of the nanogels may be a salt of alginic acid.

Alginate is composed of β-(1→4)-linked D-mannuronic acid (M) and α-(1→4)-linked L-guluronic acid (G) units. Sodium alginate has already been found of widespread use in food industry, pharmaceuticals, and many biomedical applications (e.g., wound dressing, drug delivery, and immunotherapy) due to its high biocompatibility, low cost, and mild gel-forming capacity by the addition of divalent cations (e.g., $Mg^{2+}$ and $Ca^{2+}$). However, alginate, which has linearly configured uronans (polyuronic acids) without sulfate and sulfonate groups, generally exhibits negligible anticoagulation activity. Therefore, chemical sulfation is a common approach to improve the anticoagulation efficiency of alginates (*Carbohydr. Polym.* 2011; 83: 1797-1803; *Biomacromolecules* 2014; 15: 2744-2750). Nevertheless, the improvement is limited because of the unstable biological activity and the requirement of organic solvents during the sulfation process. In addition, chemically modifying polysaccharides are complicated, and the sulfated polysaccharides are easily degraded (*Molecules* 2017; 22: 778).

In the present disclosure, the phenolic-polysaccharide nanogels are prepared by dry heating alginate, so as to obtain a carbonization product. The bottom-up synthesis of carbon quantum dots (CQDs) and carbonized polymer dots (CPDs) results in the formation of aromatic domains with diverse functional groups during their thermal synthesis processes.

Accordingly, in at least one embodiment, the cross-linked supramolecular structure formed in the nanogels of the present disclosure has at least one functional groups on the surface thereof, such as hydroxyl, ester, phenol, and carboxyl, so as to render properties for bio-applications to the nanogels.

In some embodiments, a medical composition for use in treating tumor is provided. The medical composition comprises the nanogel mentioned above and a pharmaceutically acceptable vehicle thereof.

As used herein, the term "pharmaceutically acceptable vehicle" refers to a pharmaceutically acceptable material, composition, or carrier, such as diluents, disintegrating agents, binders, lubricants, glidants, and surfactants, which do not abrogate the biological activity or properties of the active ingredient (e.g., the nanogel used herein), and is relatively non-toxic; that is, the vehicle may be administered to a subject without causing an undesirable biological effect or interacting in a deleterious manner with any of the components of the medical composition in which it is contained.

As used herein, the terms "treat," "treating," and "treatment" refer to acquisition of a desired pharmacologic and/or physiologic effect, e.g., alleviating or abrogating a disorder, disease, or condition, or one or more of the symptoms associated with the disorder, disease, or condition, or alleviating or eradicating the cause(s) of the disorder, disease, or condition itself. The effect may be prophylactic in terms of completely or partially preventing a disease or symptom thereof or may be therapeutic in terms of completely or partially curing, alleviating, relieving, remedying, or ameliorating a disease or an adverse effect attributable to the disease or symptom thereof.

As used herein, the terms "prevent," "preventing," and "prevention" refer to inclusion of a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, the term "subject" refers to a mammal, such as a human, but can also be another animal such as a domestic animal (e.g., a dog, a cat, or the like), a farm animal (e.g., a cow, a sheep, a pig, a horse, or the like) or a laboratory animal (e.g., a monkey, a rodent, a murine, a rabbit, a guinea pig, or the like). The term "patient" refers to a "subject" who is suspected to be, or afflicted with a disease or condition.

As used herein, the term "tumor" refers to proliferative tissue that overgrows or grows faster than normal tissue, and includes both benign and malignant tumors. "Benign tumors" are easier to remove and less probability of metastasis. "Malignant tumor" easily spreads to other organs through the lymphatic tissue, blood or body fluids of the human body. The commonly known "cancer" is also a malignant tumor. Malignant tumors include but are not limited to bladder cancer, bone cancer, blood cancer, breast cancer, melanoma, thyroid cancer, parathyroid cancer, bone marrow cancer, rectal cancer, throat cancer, laryngeal cancer, lung cancer, esophagus cancer, pancreatic cancer, stomach cancer, tongue cancer, skin cancer, brain tumor, uterine cancer, head and neck cancer, gallbladder cancer, oral cancer, colon cancer, anal and perianal cancers, central nervous system tumors, liver cancer, and colorectal cancer, etc.

Many examples have been used to illustrate the present disclosure. The examples below should not be taken as a limit to the scope of the present disclosure.

EXAMPLES

Materials and Methods

The materials and methods used in the following Examples 1-6 were described in detail below. The materials used in the present disclosure but unannotated herein were commercially available.

(1) Characterization of Graphene-Like Nanosheet-Embedded Polyphenolic-Alginate Nanogels (GNS/Alg-NGs)

The particle size and morphology of the Alg-NGs or GNS/Alg-NGs were analyzed using a Tecnai G2 F20 S-TWIN (Philips/FEI, Hillsboro, OG, USA) transmission electron microscopy (TEM) system operating at 200 kV. The Alg-NGs or GNS/Alg-NGs were carefully deposited on 300-mesh carbon-coated Cu grids at ambient temperature.

The hydrodynamic diameters and zeta potential (ζ-potential) of untreated sodium alginate, Alg-NGs or GNS/Alg-NGs in 5 mM sodium phosphate buffer (pH 7.4) were determined by dynamic light scattering (DLS, Zetasizer Nano ZS90, Malvern Instruments, Malvern, UK).

The photoluminescence (PL) spectra of the untreated sodium alginate, Alg-NGs or GNS/Alg-NGs in 5 mM sodium phosphate buffer (pH 7.4) were recorded using a monochromatic microplate spectrophotometer (Synergy 4 Multi-Mode; BioTek Instruments, Winooski, Vt., USA). The fluorescence quantum yields (QYs) of the untreated sodium alginate, Alg-NGs or GNS/Alg-NGs were determined by comparison with that of quinine sulfate standard (QY=54% in 0.1 M $H_2SO_4$).

Samples for X-ray diffraction (XRD) were prepared by depositing the Alg-NGs or GNS/Alg-NGs solution onto a silicon wafer, followed by drying at room temperature. XRD measurements were carried out at room temperature with an X-ray diffractometer (D/MAX 2200 VPC, Rigaku, Sendagaya, ShibuyaKu, Tokyo, Japan) with the Cu $K_{\alpha 1}$ line (λ=1.54 Å, energy=8.8 keV). X-ray photoelectron spectroscopy (XPS) was performed using an ESCALAB 250 spectrometer (VG Scientific, East Grinstead, England, UK) with Al Kα X-ray radiation as the X-ray source for excitation. Elemental analysis (EA) of the Alg-NGs or GNS/Alg-NGs was performed using a Vario EL cube analyzer (Elementar, Hanau, Germany) for C, H, and O.

Binding energies were corrected using the C1s peak at 284.6 eV as the standard. A Fourier transform infrared spectrometer (FT-IR, FT/IR-6100, JASCO, Easton, MD, USA) in transmission mode in the range of 500 $cm^{-1}$ to 4,000 $cm^{-1}$ with 16 scans was used to analyze possible functional groups existing in the Alg-NGs or GNS/Alg-NGs.

High-purity nitrogen was used for purging during the Fourier-transform infrared spectroscopy (FT-IR) measurements to minimize the interference from water vapor. Thermogravimetric analysis (TGA) and differential scanning calorimetry (DSC) were conducted using a TGA instrument (Q500, TA Instruments, New Castle, DE, USA) and a TA 2010 instrument (TA Instruments) in an air atmosphere (60 mL/min), respectively.

The viscosity was measured with a cone plate (cone spindle: CPA-40Z) viscometer (Brookfield, model DV1MLV, Middleboro, MA, USA). Cyclic voltammetry (CV) was performed in a PBS solution by using a three-electrode system composed of a glassy carbon electrode (GCE) as the working electrode, a platinum electrode as the counter electrode, and a saturated calomel electrode (SCE) as a reference electrode. Cyclic voltammetry was conducted using a potentiostat/galvanostat Autolab PGSTAT204 (Metrohm Autolab, Utrecht, the Netherlands) within the voltage range of −1.2 V to 1.2 V. The $^1$H-NMR spectrum was recorded using the Avance 600 MHz spectrometer (Bruker, Billerica, MA, USA) and referenced to the solvent signals.

(2) Agarose Gel Retardation

Sodium alginate and the obtained Alg-NGs or GNS/Alg-NGs samples (5 mg/mL; 15 μL) were separately mixed with 10% glycerol, and then analyzed by gel electrophoresis in 1.0% agarose gel and 40 mM Tris-acetate buffer/1 mM ethylenediaminetetraacetic acid (TAE buffer, pH 8.0) at 100 V for 30 min. The gel was externally stained by the positively charged methylene blue (0.1 mg/mL, 150 mL) after electrophoresis and destained in TAE buffer (pH 8.0) for 30 min.

(3) 2,2-diphenyl-1-picrylhydrazyl (DPPH) Radical Scavenging Activity

To measure the radical scavenging activity of GNS/Alg-NGs, various concentrations of untreated sodium alginate, Alg-NGs or GNS/Alg-NGs (1 μg/mL to 100 μg/mL) were added to a DPPH solution (50 μM, diluted in ethanol (EtOH)) in a mixing solution of 50% PBS and 50% EtOH, and then reacted for 30 min at room temperature. The decrease in the solution absorbance was measured at 525 nm. The percentage DPPH radical scavenging activity was calculated using the following formula:

$$\text{DPPH radical scavenging activity (\%)} = [(A_0 - A_1)/A_0 \times 100]$$

where $A_0$ and $A_1$ are the absorbance values in the absence and presence of alginate, Alg-NGs or GNS/Alg-NGs, respectively.

(4) Folin-Ciocalteu Assay

The total phenolic content of the GNS/Alg-NGs was measured by using the Folin-Ciocalteu reagent. Briefly, 40 μL of GNS/Alg-NGs were mixed with Folin-Ciocalteu reagent (240 μL) for 0.5 hours (h), and 120 μL of sodium carbonate (7.5%, w/v) was added after 0.5 h. The absorbance was then measured at 760 nm after incubation at 25° C. for an additional 0.5 h. Results were expressed as standard quercetin equivalents (μg of quercetin/μg of GNS/Alg-NGs). The Folin-Ciocalteu assay was based on the transfer of electrons from phenolic compounds in a basic solution to phosphomolybdic/phosphotungstic acid to form blue complexes [$(PMoW_{11}O_{40})^{4-}$], which were quantitated by monitoring the absorbance at 760 nm. However, the Folin-Ciocalteu assay was not only sensitive to phenolic compounds but also many reducing agents. Thus, this assay could be employed to measure the total reducing capacity of the sample.

(5) In Vitro Cytotoxicity Assay

For determining in vitro cytotoxicity of GNS/Alg-NGs, 4T1 (4T1 murine mammary cancer cell line), TRAMP-C1 (transgenic adenocarcinoma of the mouse prostate cl cell line), MDCK (Madin-Darby Canine Kidney cells), MCF10A (human breast epithelial cell line), HaCaT (human keratinocyte cell line), HUVEC (human umbilical vein endothelial cell line), HEK-293T (human embryonic kidney 293 cell line), RD (human rhabdomyosarcoma cell line), HepG2 (human liver cancer cell line), and A549 (human lung adenocarcinoma epithelial cell line) cells were used. All cell lines were obtained from American Type Culture Collection (ATCC, Manassas, VA, USA).

HUVEC and A549 cell lines were cultured in M199 and F-12K media, respectively, and HaCaT, HEK-293T, MCF10A, RD, HepG2, and TRAMP-C1 cell lines were cultured in the DMEM medium. MDCK cell lines were cultured in EMEM media. 4T1 cell lines were cultured in RPMI-1640 media. The medium was supplemented with fetal bovine serum (FBS, 10%), antibiotic-antimycotic (1%), L-glutamine (2.0 mM), and nonessential amino acids (NEAA, 1%) in 5% $CO_2$ at 37° C. The cell number was determined by the trypan blue exclusion assay (Gibco, Thermo Fisher Scientific, Waltham, MA, USA), and the cell viability was determined using the PrestoBlue assay. Briefly, approximately $1.0 \times 10^4$ cells per well of all cell lines were separately incubated with the respective culture medium for 12 h at 37° C. containing 5% $CO_2$ in 96-well plates. Then, the culture medium in each well was replaced with 100 μL of medium containing GNS/Alg-NGs (0.1 mg/mL to 1.0 mg/mL), followed by incubation for 72 h. The cells were carefully rinsed thrice with PBS and treated with the Presto-Blue reagent (ten-fold dilution, 100 μL per well) for 4 h. Then, the fluorescence intensities (IF590) were measured at an excitation/emission wavelength of 540/590 nm (Synergy 4 Multi-Mode; BioTek Instruments, USA). Because fluorescence intensity was directly correlated with cell number, the cell viability in the control group (media without GNS/Alg-NGs) was assumed to be 100%.

(6) Hemolysis Assays

The human red blood cells (RBCs) for the hemolysis assays were donated from MacKay Memorial Hospital (MMH Taipei, Taiwan). Blood samples were collected from a healthy volunteer (male, 25 years old) into tubes containing ethylenediaminetetraacetic acid (EDTA) and immediately (within 30 min of the collection) centrifuged (relative centrifugal force (RCF) 3,000 g, 10 min, 4° C.) to remove the serum. The RBCs were diluted with sterile isotonic physiological buffer to obtain an RBC stock suspension (about 4.0 vol % blood cells). For the analysis, 100 μL of the RBC stock suspension was incubated with aliquots of GNS/Alg-NGs dispersions (0.1 mg/mL to 1.0 mg/mL) in 1.5 mL vials at 37° C. for 1 h. Then, the aliquot samples were centrifuged at an RCF of 1,000 g for 10 min. Hemolysis was measured based on the absorption of hemoglobin at 576 nm ($OD_{576}$) in the supernatant (200 μL). For the 0% hemolysis reference ($OD_{576\ blank}$), a sterile isotonic physiological buffer was used. The positive control expressing 100% hemolysis was prepared by adding ultrapure water to an RBC suspension ($OD_{576\ ultrapure\ water}$). The hemolysis activity was calculated as follows:

Hemolysis (%)=$[(OD_{576\ GNS/Alg-NGs} - OD_{576\ blank})/(OD_{576\ ultrapure\ water} - OD_{576\ blank})] \times 100\%$.

(7) Wound Healing Assay

4T1 breast cancer cells were seeded into a 2-well insert culture chamber (Ibidi, Germany) in 24-well at a density of $1.2 \times 10^4$/well at 37° C. After the cells were attached to 24-well, the insert was removed using sterilized forceps, and a gap was exposed in the middle. After taking pictures with a microscope at 0 h, 500 μL of RPMI medium without sample (10% FBS) (control group), RPMI medium with different samples (alginate, Alg-NGs or GNS/Alg-NGs) were respectively injected for incubating 12 hours and then photographed, and ImageJ analysis software was used to analyze the cell-free areas in the gap that were not yet occupied by cancer cells. Migration rate %=[(cell-free $area_{0\ hours}$–cell-free $area_{12\ hours}$)/cell-free $area_{0\ hours}$]×100%.

(8) Cancer Cell Invasion Assay

In a 24-well cell culture plate (Boyden transwell chamber) (BD Falcon, MA, USA) with an 8 μm pores polycarbonate membrane insert, 100 μL of growth factor reduced Matrigel (200 μg/mL, Corning, USA) was applied to the top of the membrane for two hours. Then, 700 μL of culture medium (containing 10% FBS) was added to the 24-well cell culture plate, and the membrane insert was inserted to the 24-well cell culture plate. Afterward, $10^5$ CFU of 4T1 cells were added to the culture medium (containing 2% FBS) in the upper chamber, while the culture medium containing 10% FBS was added to the lower chamber as a chemoattractant. In the meantime, different samples (alginate, Alg-NGs or GNS/Alg-NGs) were separately added to the upper chamber and incubated for 24 hours. Next, the cells on the top surface of the membrane were gently wiped off with a cotton swab. The invasive cells that reached the bottom of the membrane were stained with Hoechst Fluorescent Nucleic Acid Stain (Hoechst 33342) for 20 minutes, and then monitored and quantified under the dark field of a fluorescent microscope (Olympus IX-71, USA), and the results of three independent experiments were statistically analyzed using Student's t-test and ANOVA ($p<0.05$)

(9) Animal Experiment for Antitumor/Anti-Metastasis

Figure 19A:
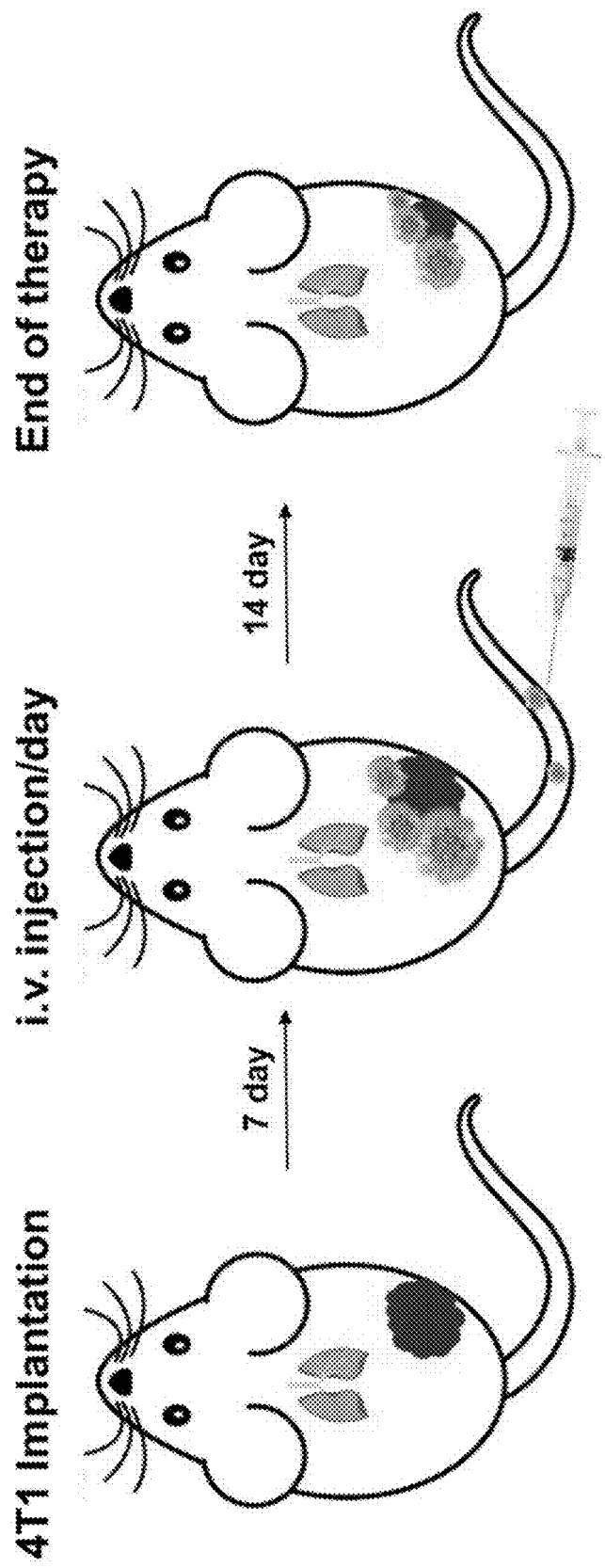
FIG. 19A is a schematic diagram illustrating the experimental protocol of the mouse animal model in Example 6 of the present invention.

In FIG. 19A, approximately $10^6$ cells of 4T1 cell line (1×PBS) were inoculated with a 30G insulin needle in the fourth mammary fat pad of 5-week-old BALB/c female mice (18-24 g). Approximately seven days later, when the mammary tumor volume reached 80-100 mm³, the mice were divided into three groups (6 mice in each group), and each group was received PBS (control group), GNS/Alg-NGs-270 (dose 50 mg/kg) or GNS/Alg-NGs-270 (dose 100 mg/kg) respectively via tail vein injection daily for 2 weeks, respectively. The tumor size was measured using a vernier caliper every day and the tumor volume was calculated according to the formula: tumor volume (mm³)=½[(tumor length)×(tumor width)²]. Two weeks later, the mice were euthanized, and major organs including the heart, liver, spleen, lung, and kidney were harvested and stained with hematoxylin and eosin (H&E). Lungs were fixed with Bouin's solution and the number of nodules on the surface was counted and the size of each nodule was measured. Murine Carcinosis Index (MCI)=maximum nodule diameter score×nodule number score, wherein each parameter can be determined through the following table A.

TABLE A

Parameter Lookup Table of the murine carcinosis index (MCI)

| Maximal nodule Diameter | No visible disease | <0.5 mm | ≥0.5 & <2 mm | ≥2 mm | | |
|---|---|---|---|---|---|---|
| Diameter score | 0 | 1 | 5 | 10 | | |
| Nodule number | 1-5 | 6-10 | 11-15 | 16-20 | 21-25 | >25 |
| Number score | 1 | 2 | 3 | 4 | 5 | 6 |

Example 1: Synthesis of Graphene-Like Nanosheet (GNS)-Embedded Polyphenolic Alginate Nanogels (GNS/Alg-NGs)

As show in FIG. 1, the graphene-like nanosheet-embedded polyphenolic-alginate nanogels (hereinafter referred to as "GNS/Alg-NGs") was synthesized from sodium alginate by heating. Briefly, 50 mg of sodium alginate was placed in a 20 mL glass sample bottle, and dry heated in a laboratory-grade convection oven (DH 300, Dengyng, Taiwan) at 150° C., 180° C., 210° C., 240° C., 270° C., or 300° C. for 3 h. The as-obtained solid product was allowed to cool down and then dissolved in 5.0 mL of deionized water by sonication for 1 h. The larger particles were removed by centrifugation at a relative centrifugation force (RCF) of 500 g for 30 min. The as-obtained GNS/Alg-NGs dispersions were stored at 4° C. for future use.

The alginate nanogels (hereinafter referred to as "Alg-NGs") or GNS/Alg-NGs obtained after dry heating at 150° C., 180° C., 210° C., 240° C., 270° C., or 300° C. were denoted as Alg-NGs-150, Alg-NGs-180, GNS/Alg-NGs-210, GNS/Alg-NGs-240, GNS/Alg-NGs-270, and GNS/Alg-NGs-300, respectively. The product yields range from about 95% to about 36% (as shown in Table 1 below).

Example 2: Characterization of Nanogels

The characterizations of the Alg-NGs or GNS/Alg-NGs dispersions obtained in Example 1 were performed and reported as follows.

(1) Solubility and Viscosity

Figure 2:
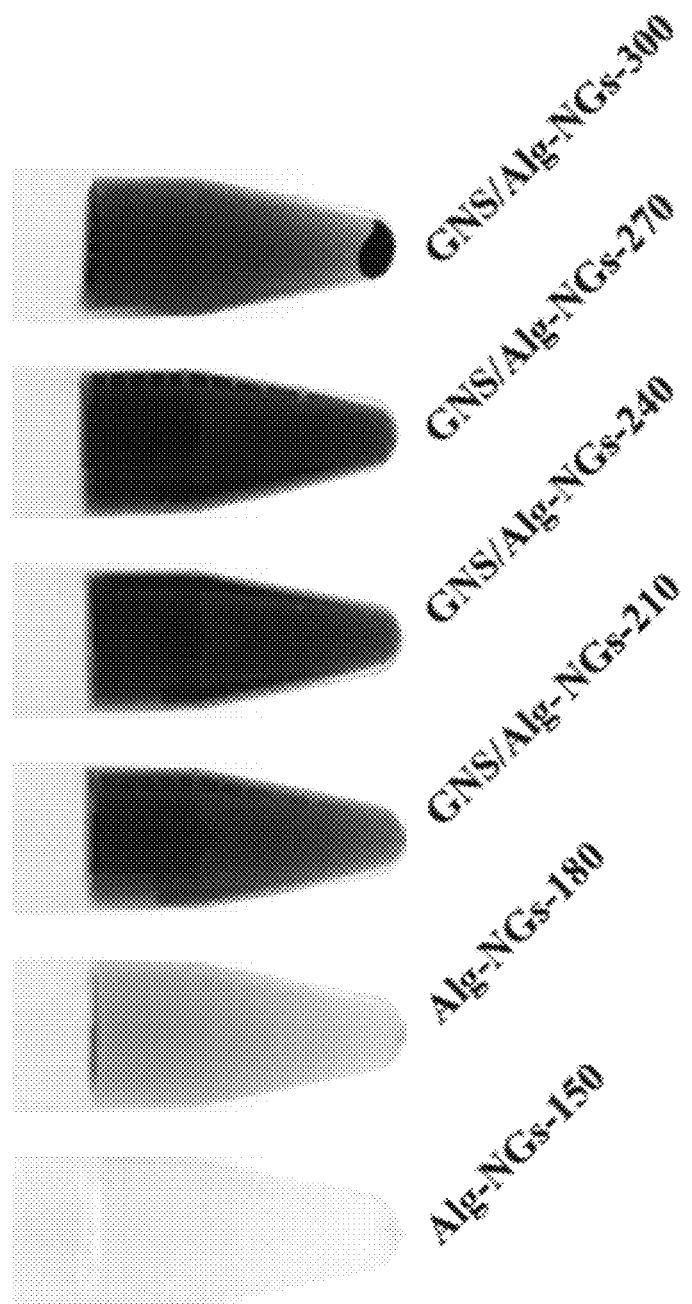
FIG. 2 shows the photographs of the dispersions in deionized water of Alg-NGs-150, Alg-NGs-180, GNS/Alg-NGs-210, GNS/Alg-NGs-240, GNS/Alg-NGs-270, and GNS/Alg-NGs-300 after centrifugation progress.

Firstly, in view of solubility, all of the dispersions except for GNS/Alg-NGs-300 have high solubility in water (>50 mg/mL) at 25° C., as shown in FIG. 2. Further, at 25° C., sodium alginate solution has high viscosity (442.2 mPas, 10 mg/mL), whereas most Alg-NGs and GNS/Alg-NGs have low viscosity even at five times higher concentration (<5.2 mPas, 50 mg/mL). The decreased viscosity of the heated products suggested that the polymeric characteristics of alginate were destroyed after heating.

(2) Hydrodynamic Diameter and Zeta Potential

Referring to Table 1 below, the hydrodynamic diameters of Alg-NGs or GNS/Alg-NGs synthesized at 150° C. to 300° C. showed a decrease from 410.2 nm to 52.0 nm, due to higher decomposition and carbonization with increasing temperature. Further, the hydrodynamic diameter of Alg-NGs-150 (410.2 nm) was only slightly smaller than that of untreated sodium alginate (474.6 nm), indicating that no significant pyrolysis occurred when heated at 150° C. Compared to GNS/Alg-NGs-270, GNS/Alg-NGs-300 exhibited larger hydrodynamic size (198.2 nm), due to over-crosslinking and carbonization.

negatively charged carboxylic groups on the C-6 position of the monomeric units. In comparison, the Alg-NGs and GNS/Alg-NGs exhibited zeta potential values of about −46 mV to about −30 mV, as a result of the dehydration, condensation of hydroxyl groups and carboxylic groups, and carbonization.

Figure 3:
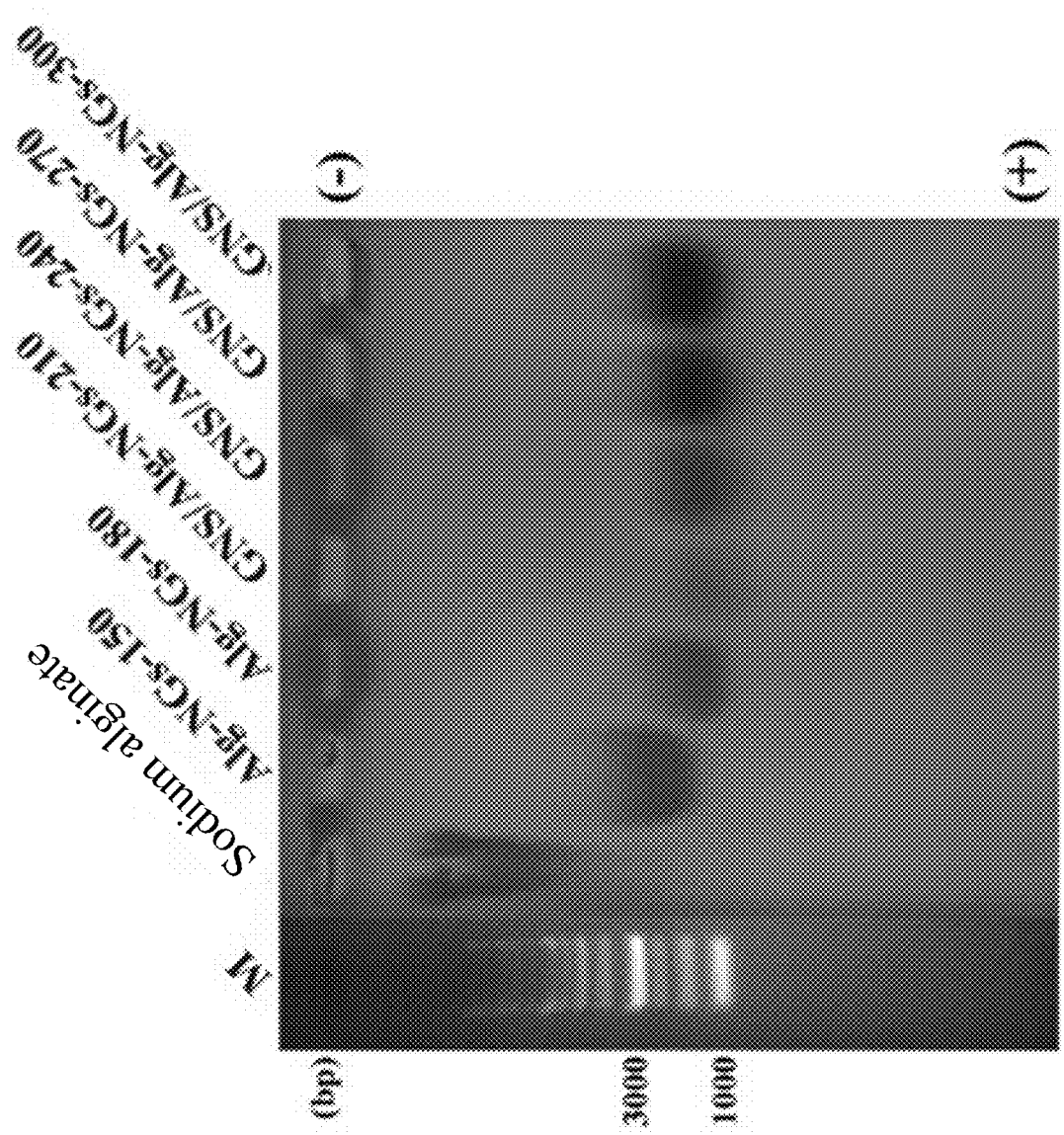
FIG. 3 shows the charge and size distribution of sodium alginate, Alg-NGs-150, Alg-NGs-180, GNS/Alg-NGs-210, GNS/Alg-NGs-240, GNS/Alg-NGs-270, and GNS/Alg-NGs-300 measured by agarose gel electrophoresis assay.

The size distributions of the Alg-NGs and GNS/Alg-NGs were further confirmed by agarose gel electrophoresis assay, and the results were shown in FIG. 3. It was observed that the size distributions of Alg-NGs and GNS/Alg-NGs were in agreement with the hydrodynamic diameters and zeta potential values thereof as disclosed above.

(3) Transmission Electron Microscopy (TEM) Images

Figure 4A:
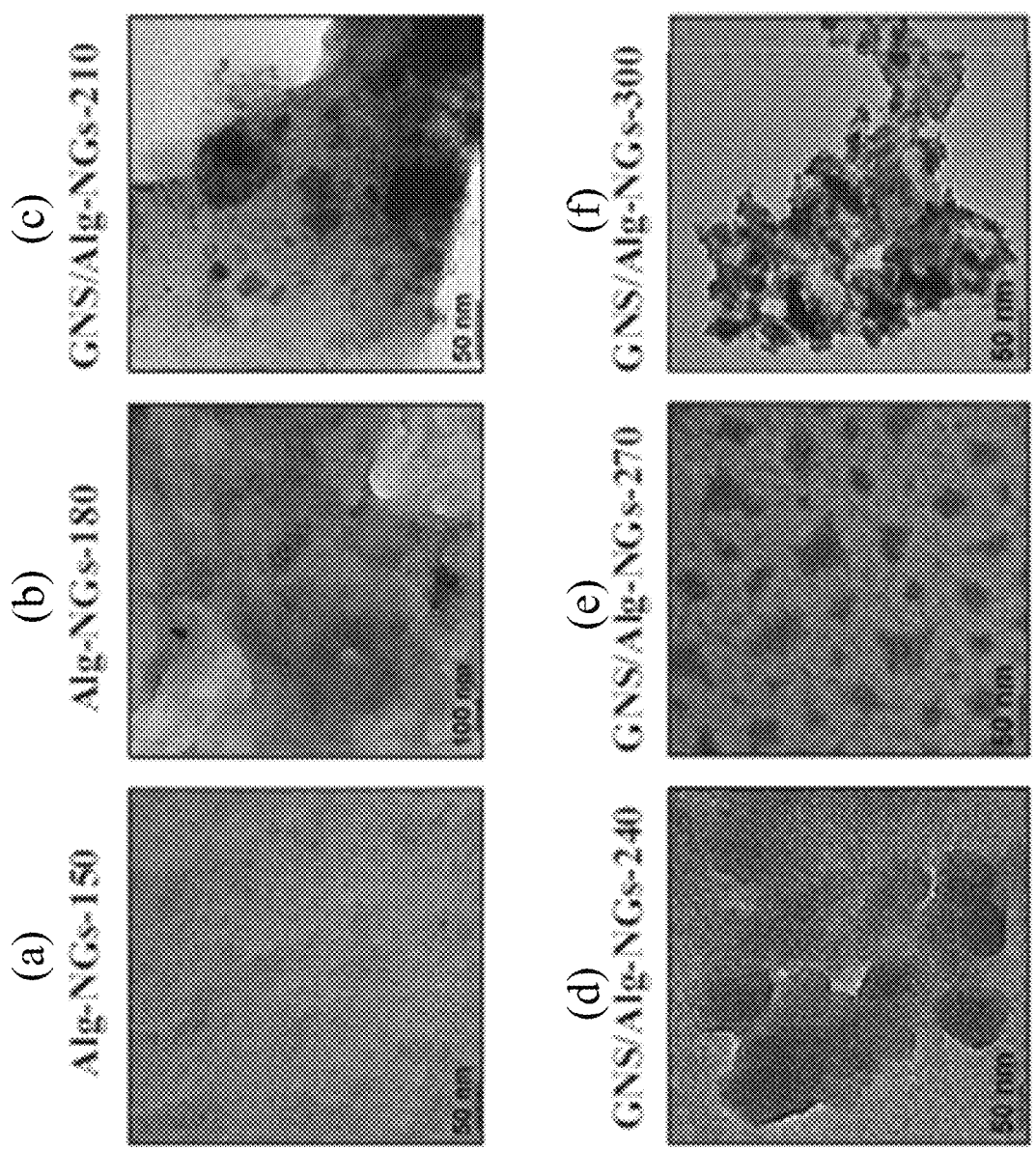
FIGS. 4A and 4B show the transmission electron microscopy (TEM) images and the high-resolution transmission electron microscopy (HRTEM) images of the (a) Alg-NGs-150, (b) Alg-NGs-180, (c) GNS/Alg-NGs-210, (d) GNS/Alg-NGs-240, (e) GNS/Alg-NGs-270 and (f) GNS/Alg-NGs-300 synthesized at different temperatures, respectively.

By the TEM images shown in FIG. 4A, it was confirmed that Alg-NGs-150 and Alg-NGs-180 contained gel-like crosslinking polymers formed by condensation reactions. In contrast, the GNS/Alg-NGs heated at 210° C. to 300° C. exhibited distinct particles that form along with polymer matrix. It is noted that the TEM image of the GNS/Alg-NGs-270 revealed a particle size with a mean diameter of 48.7±6.5 nm (100 counts). In contrast, relatively low solubility (<0.1 mg/mL) and large-sized carbon particles were observed in GNS/Alg-NGs-300, due to a higher degree of carbonization of sodium alginate.

Figure 4B:
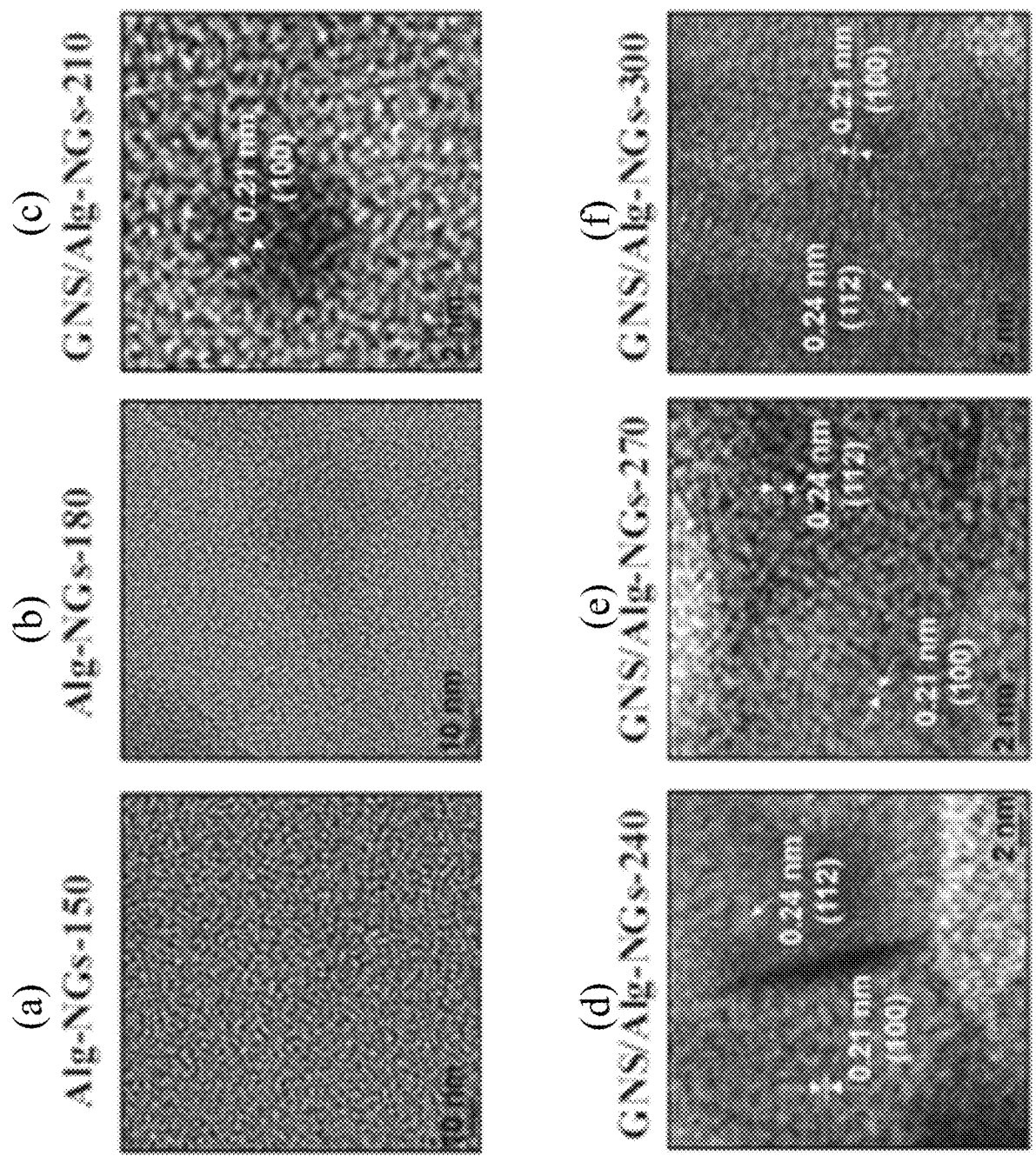

High-resolution TEM (HRTEM) images shown in FIG. 4B further demonstrated d-spacing values of 0.21 nm and 0.24 nm in the carbonized products, which were attributed to the lattice planes of the (100) and (112) facets of graphene-inter-planar spacing, respectively, and revealed the formation of crystalline graphene-like structures in addition to the cross-linked nanogel matrix. Alg-NGs-150 and Alg-NGs-180 did not show lattice planes in the HRTEM images, however, thereby indicating no formation of a crystalline carbon core formation during heating at low temperatures.

(4) UV-Visible Absorption Spectra

Figure 5A:
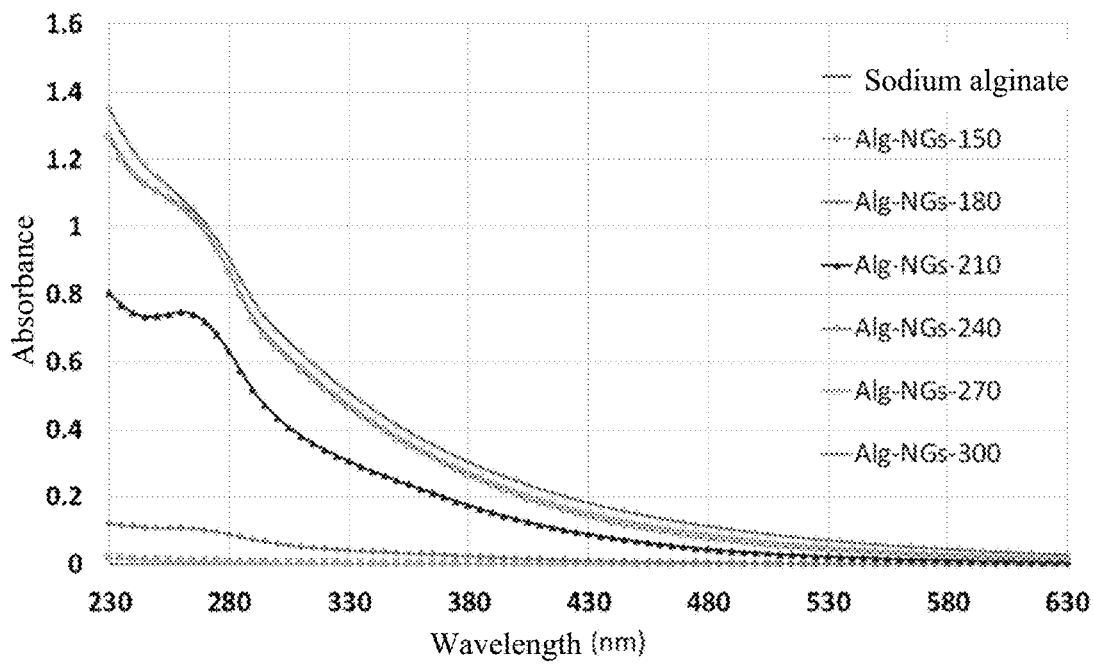
FIGS. 5A and 5B show the UV-vis absorption and the fluorescence spectra of sodium alginate, Alg-NGs-150, Alg-NGs-180, GNS/Alg-NGs-210, GNS/Alg-NGs-240, GNS/Alg-NGs-270 and GNS/Alg-NGs-300, respectively.

Referring to FIG. 5A, UV-visible absorption spectra showed an absorption band at 280 nm for all Alg-NGs and GNS/Alg-NGs, except for Alg-NGs-150. This band corresponded to the $\pi \rightarrow \pi^*$ transitions of conjugated C=C bonds (sp$^2$ clusters), and indicated the formation of graphitic carbon during carbonization of sodium alginate. A shoulder band was observed at 320 nm to 360 nm for Alg-NGs-180 and all of the GNS/Alg-NGs, and ascribed to the $n \rightarrow \pi^*$ edge transitions of C=O bonds and/or interlayer $\pi \rightarrow \pi^*$ charge transfer, supporting the presence of oxygen-containing func-

TABLE 1

Product yield and characteristics of the dispersions prepared from sodium alginate without treatment and after dry heating

|  | Product yield | Zeta potential | Hydrodynamic diameter | Fluorescence quantum yield | Elemental compositions (wt %)[b] | | |
| --- | --- | --- | --- | --- | --- | --- | --- |
|  | (%) | (mV; n = 5) | (nm; n = 5) | (QY) (%)[a] | C | H | O |
| Sodium alginate | — | −86.2 ± 2.1 | 474.6 ± 155.7 | <0.01 | 29.98 | 5.02 | 55.33 |
| Alg-NGs-150 | 95.2 | −45.8 ± 1.3 | 410.2 ± 77.9 | <0.01 | 29.38 | 5.20 | 55.63 |
| Alg-NGs-180 | 85.3 | −41.8 ± 2.4 | 327.4 ± 65.3 | 14.30 | 30.74 | 5.00 | 54.61 |
| GNS/Alg-NGs-210 | 60.9 | −40.5 ± 6.9 | 153.1 ± 38.4 | 8.30 | 36.71 | 4.63 | 46.16 |
| GNS/Alg-NGs-240 | 48.3 | −34.2 ± 4.2 | 78.5 ± 25.7 | 4.48 | 34.83 | 4.88 | 45.48 |
| GNS/Alg-NGs-270 | 46.8 | −31.7 ± 5.1 | 52.0 ± 11.3 | 3.22 | 33.53 | 4.81 | 44.57 |
| GNS/Alg-NGs-300 | 36.1 | −30.4 ± 0.8 | 198.2 ± 49.9 | 2.09 | 35.19 | 3.92 | 44.00 |

[a]compared to quinine sulfate (QY: 54% in 0.1M $H_2SO_4$).
[b]determined by elemental analysis.

Next, as shown in Table 1 above, the zeta potential of untreated sodium alginate was about −86 mV, because of its tional groups on the Alg-NGs-180 and GNS/Alg-NGs. It was further observed that sodium alginate underwent a higher degree of carbonization at 240° C. to 300° C., leading to the formation of a larger graphitic carbon network resulting in strong π→π* transitions of C=C bonds.

Figure 5B:
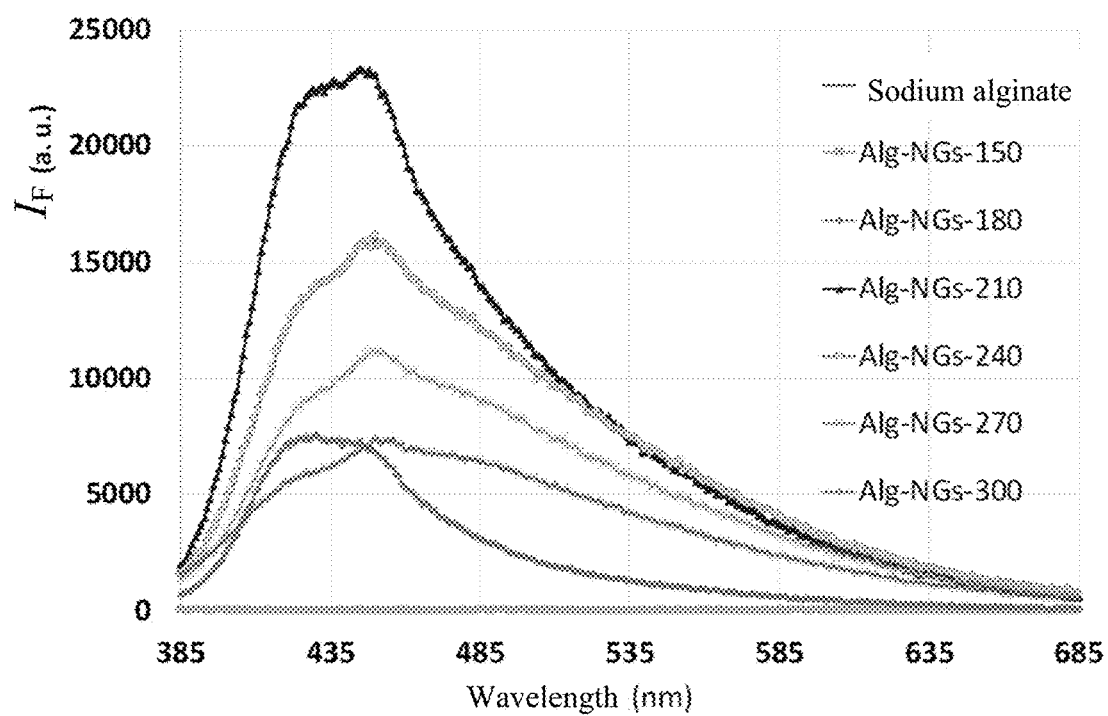

Next, the fluorescence spectra were examined. Upon excitation with a wavelength of 365 nm, the GNS/Alg-NGs exhibited a broad fluorescence band centered at about 450 nm (FIG. 5B). The strong fluorescence of the Alg-NGs and GNS/Alg-NGs prepared at 150° C. to 210° C. might be due to the as-formed graphene-like nanosheets embedded in the cross-linking polymer matrix of the nanogels (as shown in Table 1 and FIG. 5B). The lower fluorescence intensity of GNS/Alg-NGs prepared at >210° C. was mainly due to the higher degree of carbonization, which was evident from the decreased oxygen content for GNS/Alg-NGs with increasing synthesis temperature (Table 1).

(5) X-ray Diffraction (XRD) Spectra

Figure 6:
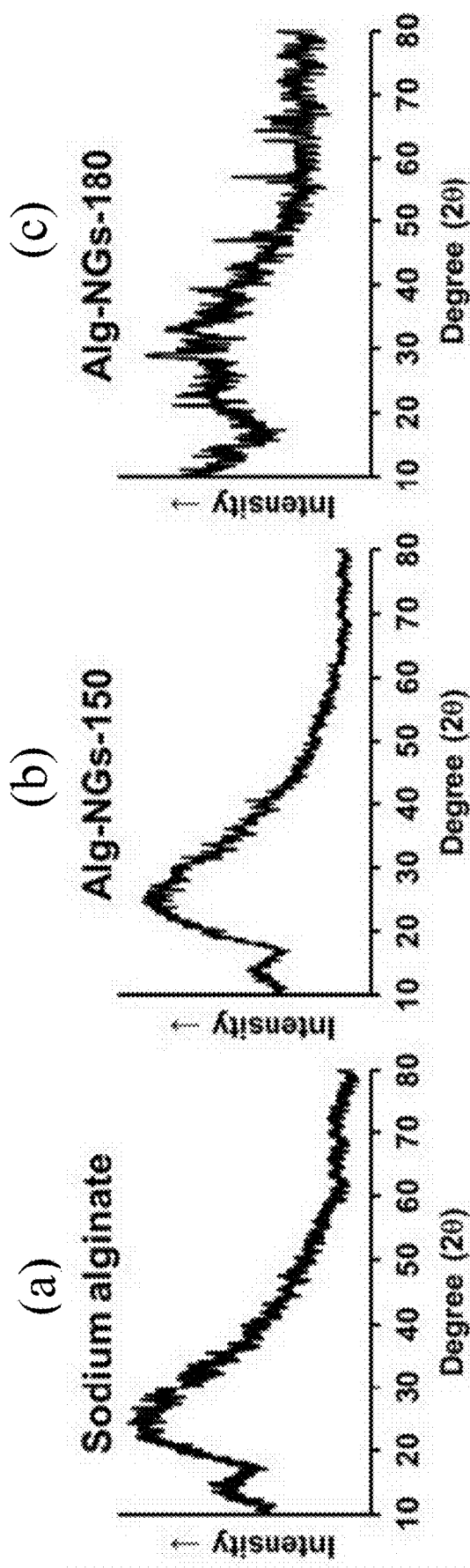
FIG. 6 shows the X-ray diffraction (XRD) spectra of (a) sodium alginate, (b) Alg-NGs-150, (c) Alg-NGs-180, (d) GNS/Alg-NGs-210, (e) GNS/Alg-NGs-240, (f) GNS/Alg-NGs-270 and (g) GNS/Alg-NGs-300.
Figure 6:
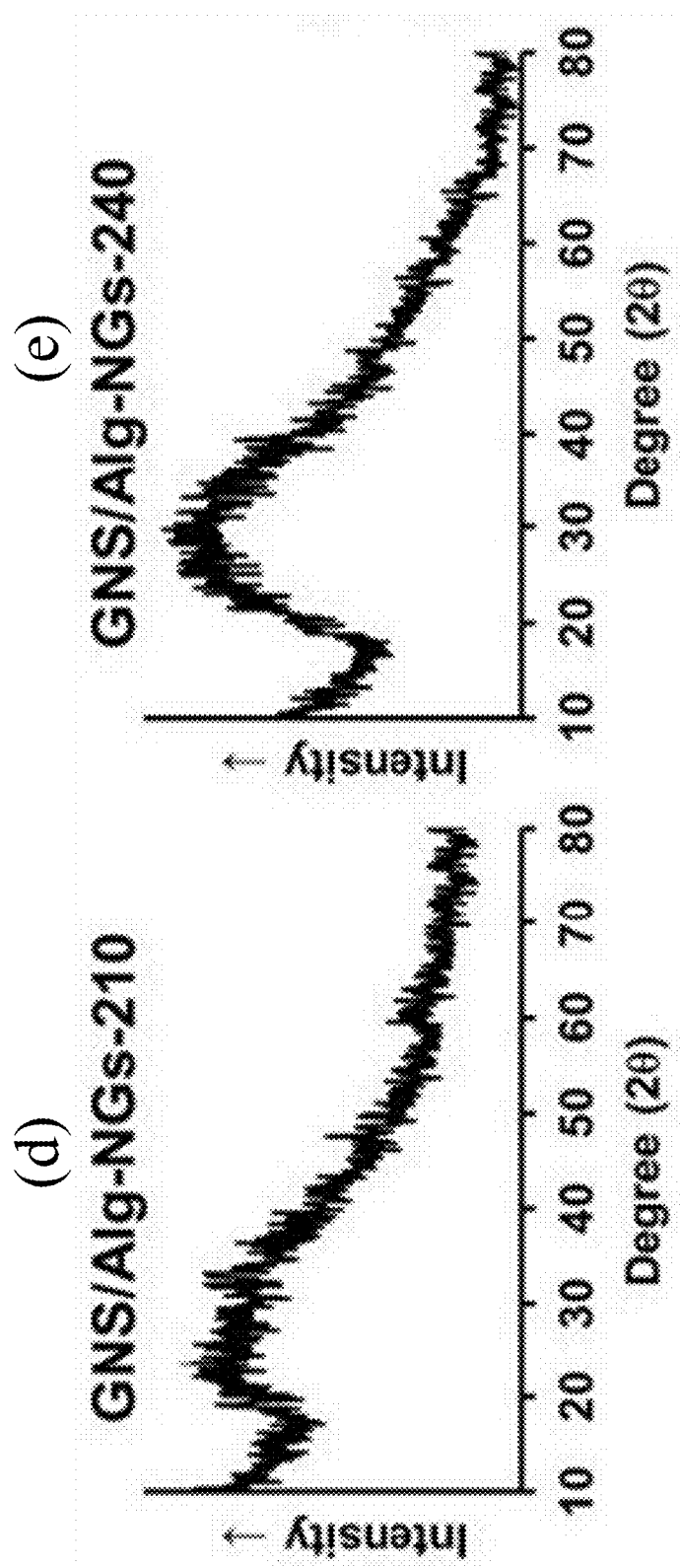
Figure 6:
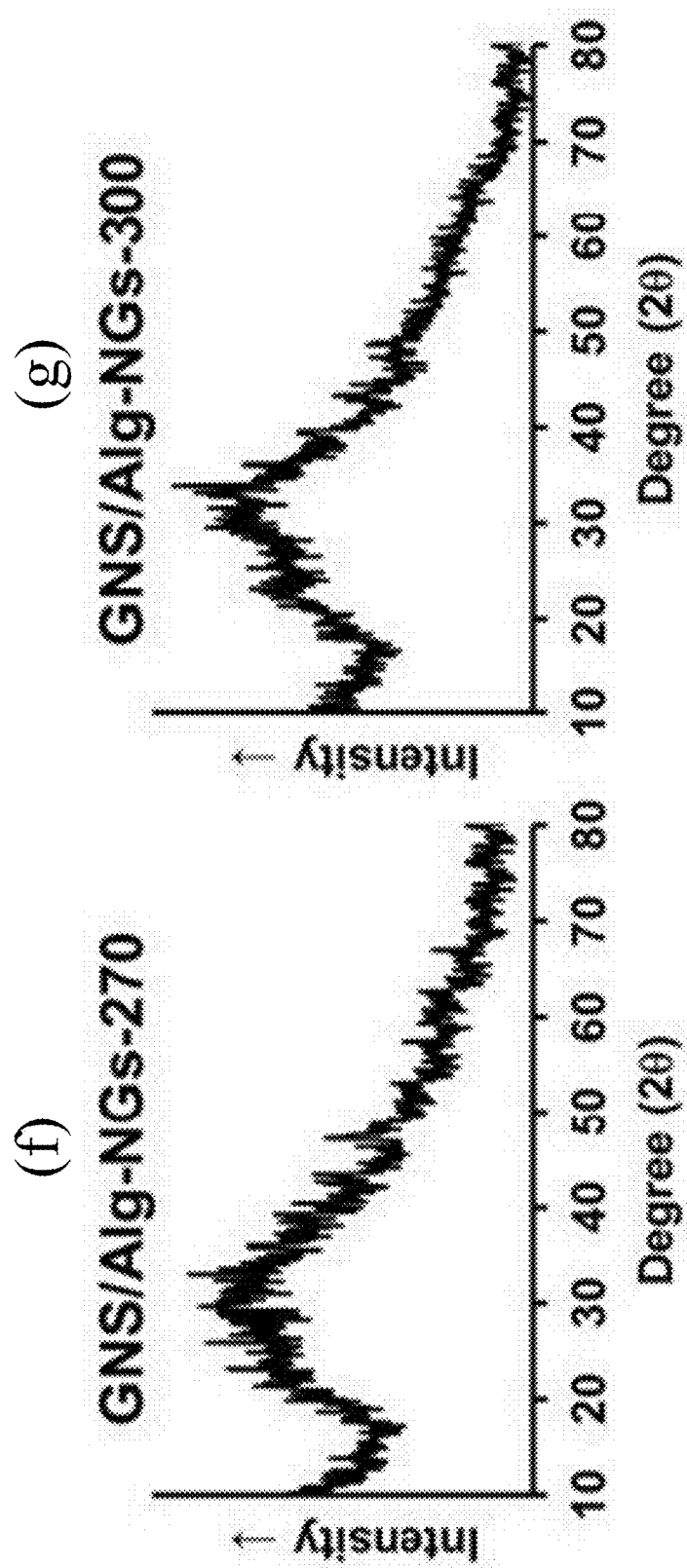

As shown in FIG. 6, the XRD spectra of sodium alginate, Alg-NGs, and GNS/Alg-NGs revealed that significant changes occurred in the alignment of crystalline polyguluronate (G form) units of sodium alginate upon heating. While most of the G form characteristics were preserved in the Alg-NGs-150, inter-planar spacing (002) of 0.33 nm corresponding to facets of graphene-like carbon structure appeared at higher temperatures (>210° C.) and the characteristic G form peak disappeared, indicating partial carbonization of sodium alginate.

Figure 7A:
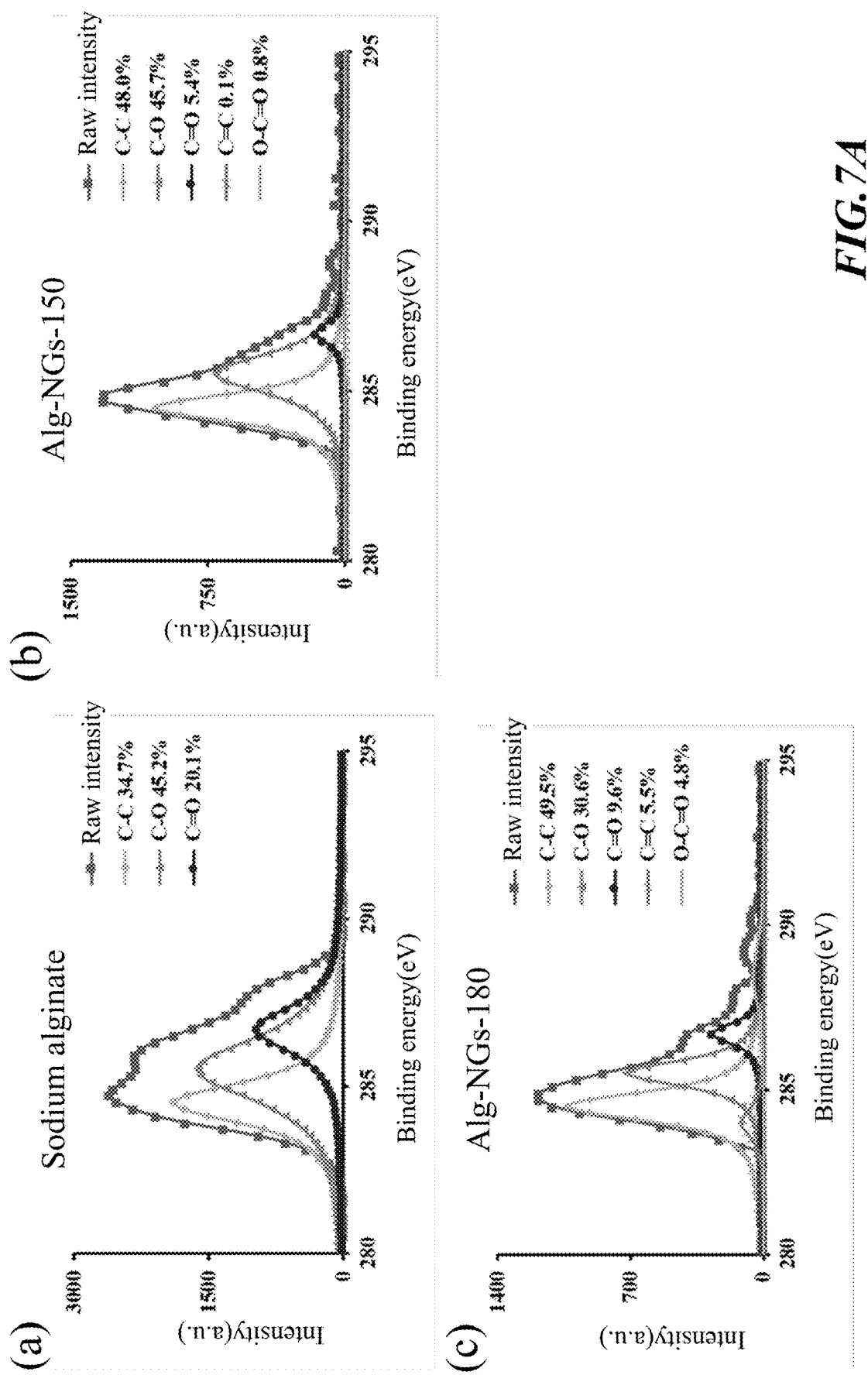
FIGS. 7A and 7B show the C1s XPS spectra and the O1s XPS spectra of (a) sodium alginate, (b) Alg-NGs-150, (c) Alg-NGs-180, (d) GNS/Alg-NGs-210, (e) GNS/Alg-NGs-240, (f) GNS/Alg-NGs-270 and (g) GNS/Alg-NGs-300 detected by X-ray photoelectron spectroscopy (XPS), respectively.
Figure 7A:
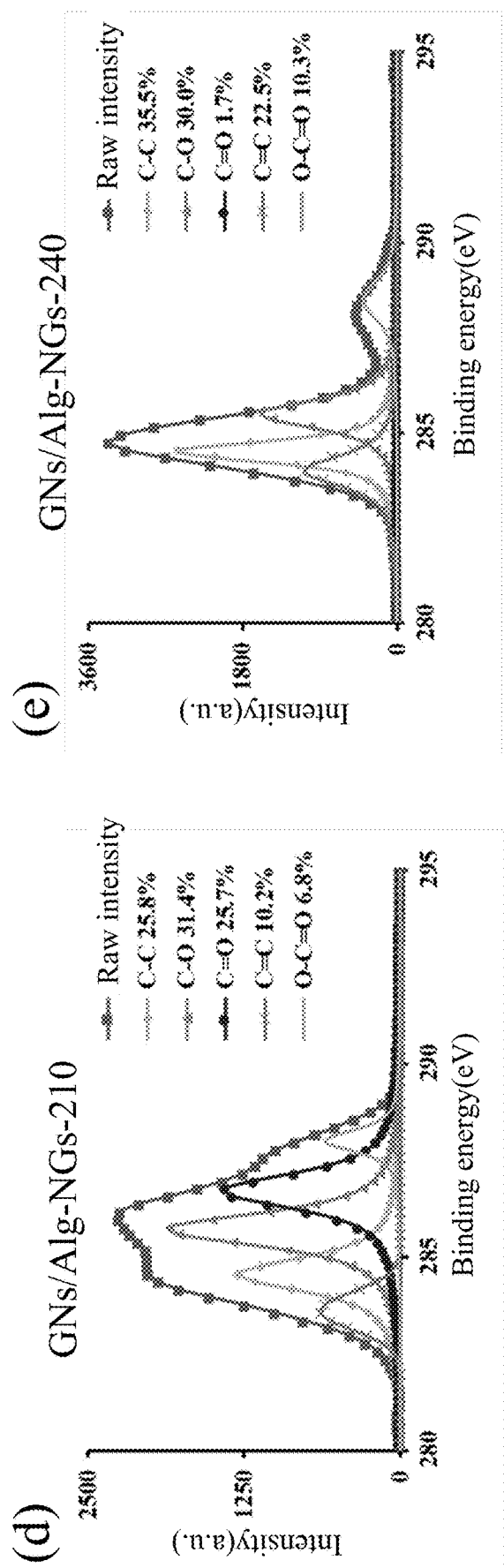
Figure 7A:
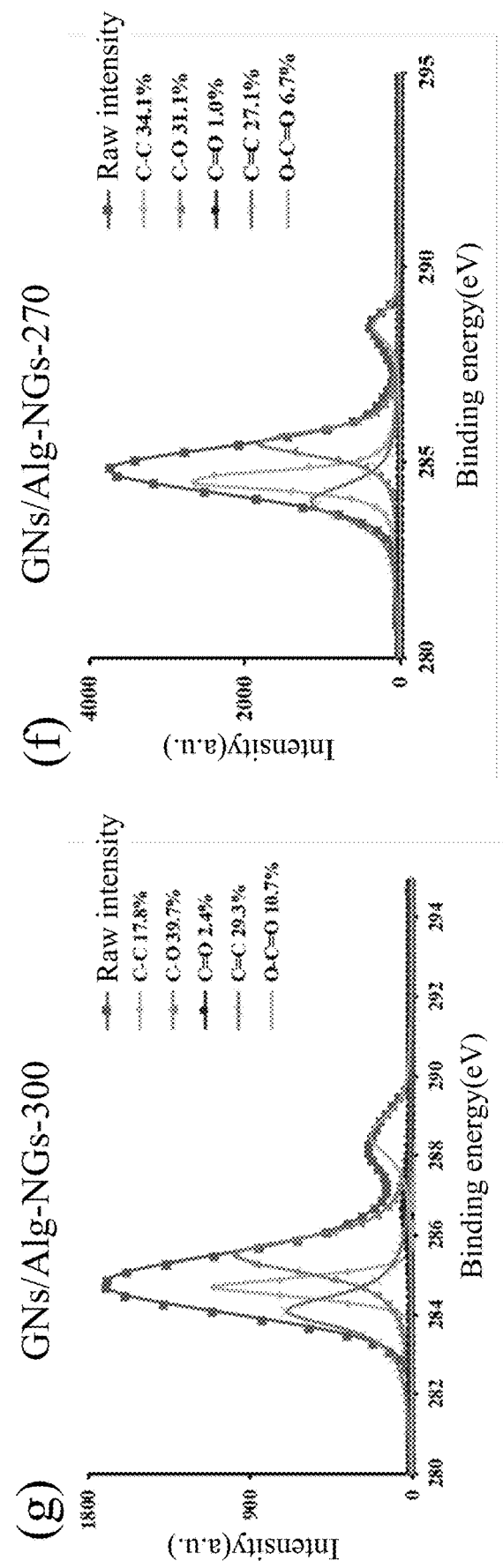
Figure 7B:
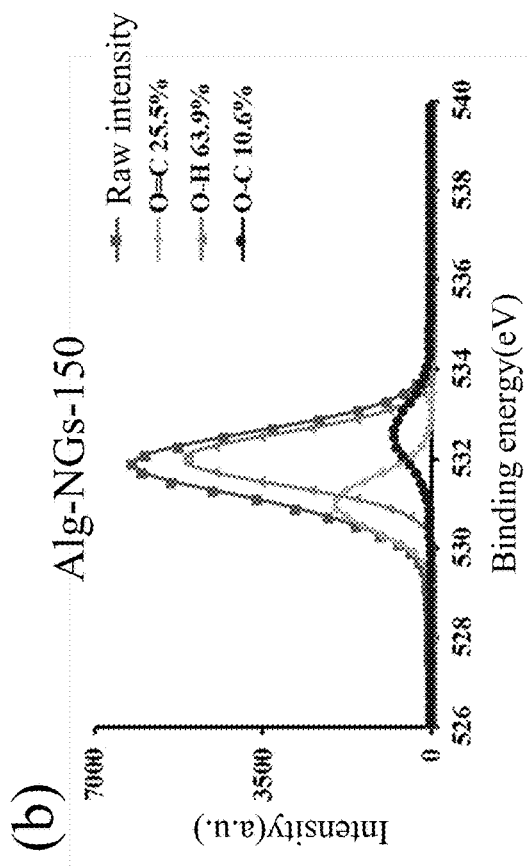
Figure 7B:
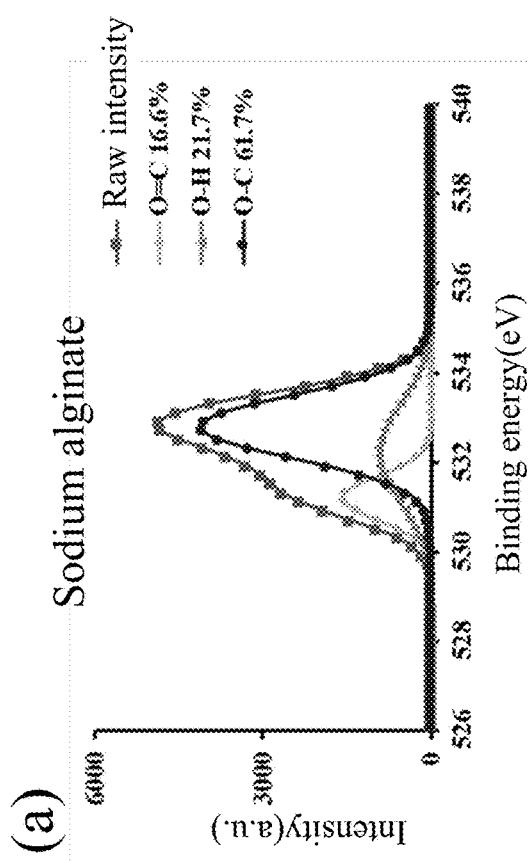
Figure 7B:
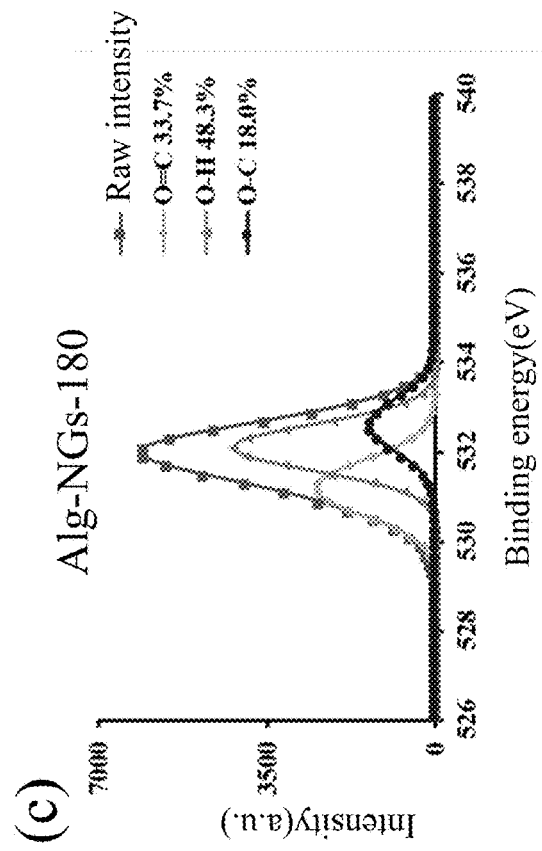
Figure 7B:
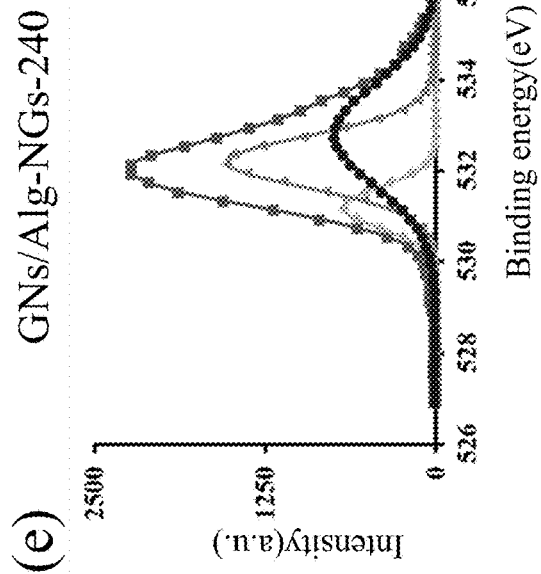
Figure 7B:
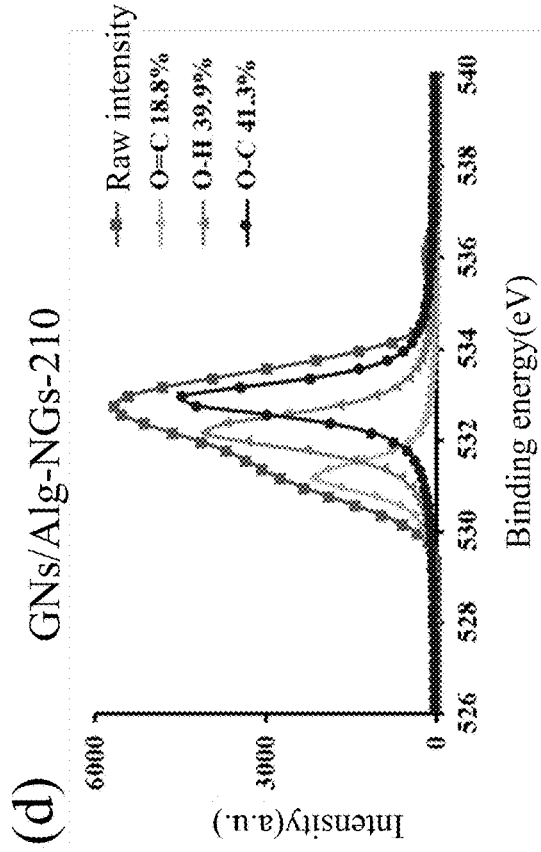
Figure 7B:
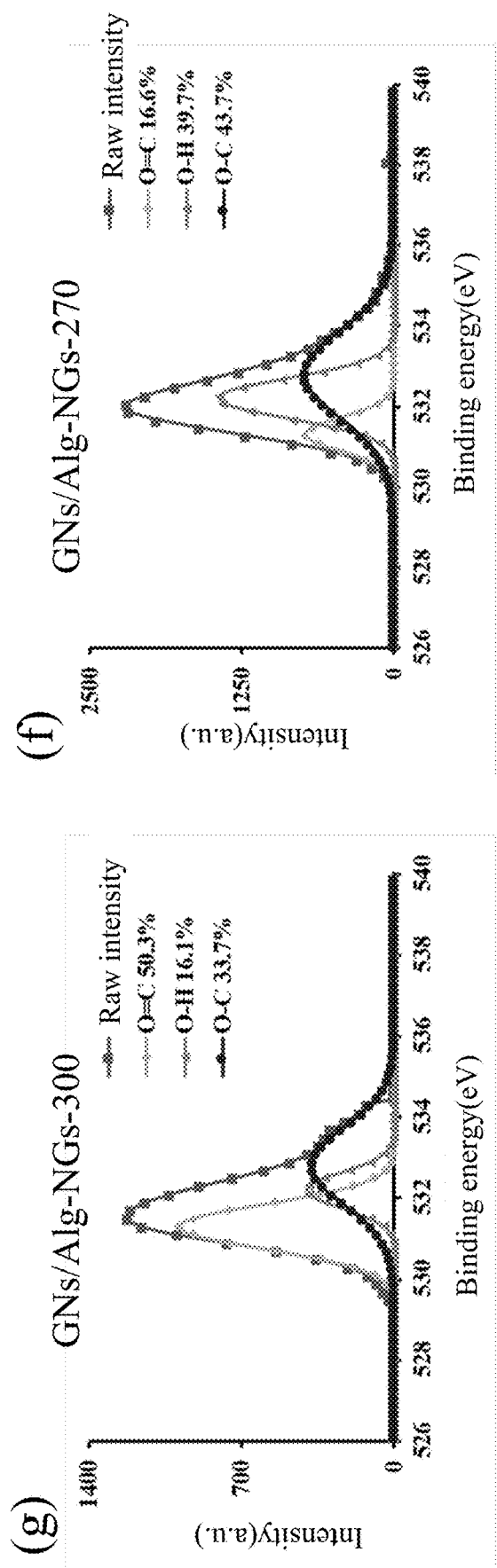

Deconvolution of the C1s spectra obtained by X-ray photoelectron spectroscopy (XPS) of untreated sodium alginate revealed three types of carbon bonds, viz. C—C (284.5 eV; 34.7%), C—O (285.5 eV; 45.2%), and C=O (286.7 eV; 20.1%), as shown in FIG. 7A. For Alg-NGs-150 and Alg-NGs-180, the percentage of C=O bonds decreased to about 5% to 10%, and ester O—C=O (288.5 eV) bonds appeared, due to the condensation reactions. Moreover, the C=C (284.0 eV, about 0.1% to about 29.3%) and O—C=O (about 0.8% to about 10.7%) bonds in Alg-NGs and GNS/Alg-NGs exhibited an increasing trend with synthesis temperatures from 210° C. to 300° C. (FIG. 7A), indicating the formation of the ester bond and sp² carbons in the alginate nanogel structures. Ester bonds were formed through the condensation process between hydroxyl and carboxylic acid groups of the alginate. Similarly, the deconvolution of the O1s XPS spectra of Alg-NGs and GNS/Alg-NGs showed three peaks at 531.2 eV, 532.2 eV, and 532.8 eV, which revealed three types of oxygen bonds, O=C, O—H, and O—C, respectively (FIG. 7B). These results indicated that the Alg-NGs and GNS/Alg-NGs had plenty of hydrophilic groups on their surfaces, such as carboxylic and hydroxyl moieties, which enhanced their aqueous solubility.

(6) Fourier-Transform Infrared Spectroscopy (FT-IR)

Figure 8:
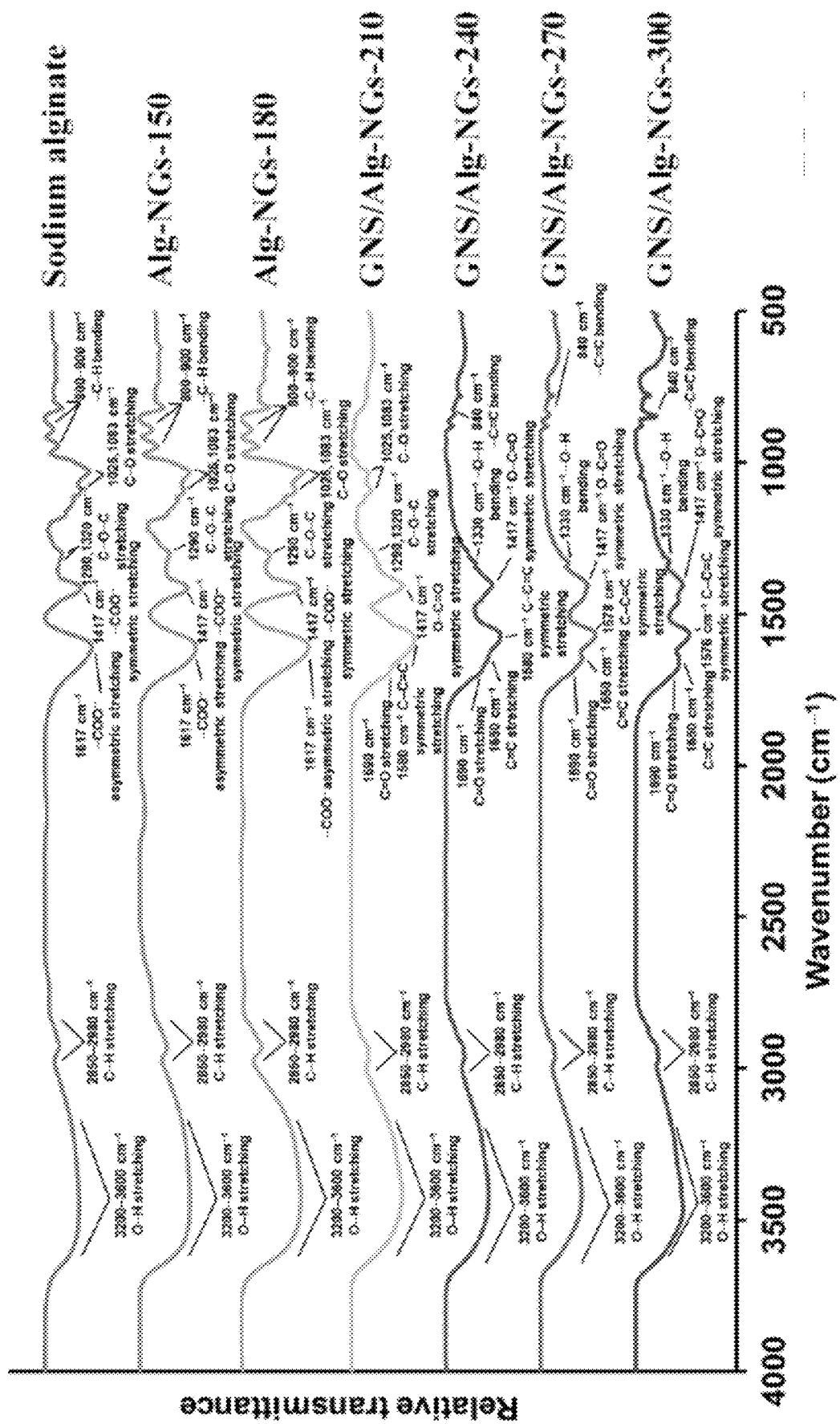
FIG. 8 shows the FT-IR spectra of sodium alginate, Alg-NGs-150, Alg-NGs-180, GNS/Alg-NGs-210, GNS/Alg-NGs-240, GNS/Alg-NGs-270 and GNS/Alg-NGs-300 detected by Fourier transform infrared spectroscopy (FT-IR).

As shown in FIG. 8, the FT-IR spectra showed peaks at 1290 and 1320 cm⁻¹, which corresponded to the D-mannuronic (M) and L-guluronic acid (G) moieties of sodium alginate, respectively. The FT-IR spectra of Alg-NGs-150 and Alg-NGs-180 revealed that they had similar chemical structures with that of sodium alginate, due to low carbonization at low temperatures. Upon increasing the synthesis temperature from 210° C. to 300° C., the C—O stretching peak at 1025/1083 cm⁻¹ decreased significantly, and a —C=C bending peak at 840 cm⁻¹ appeared from 240° C. onwards, thereby indicating the occurrence of carbonization reactions at higher temperatures. Furthermore, the spectrum of GNS/Alg-NGs-270 had a peak at 1330 cm⁻¹, which was attributed to the —O—H bending of phenol groups formed by mild aromatization during the carbonization process. Thus, these results suggested that sodium alginate underwent mild carbonization, whereby some functional groups were preserved and new functional groups were formed.

(7) Time Course of the Structure Formation of GNS/Alg-NGs

Figure 9:
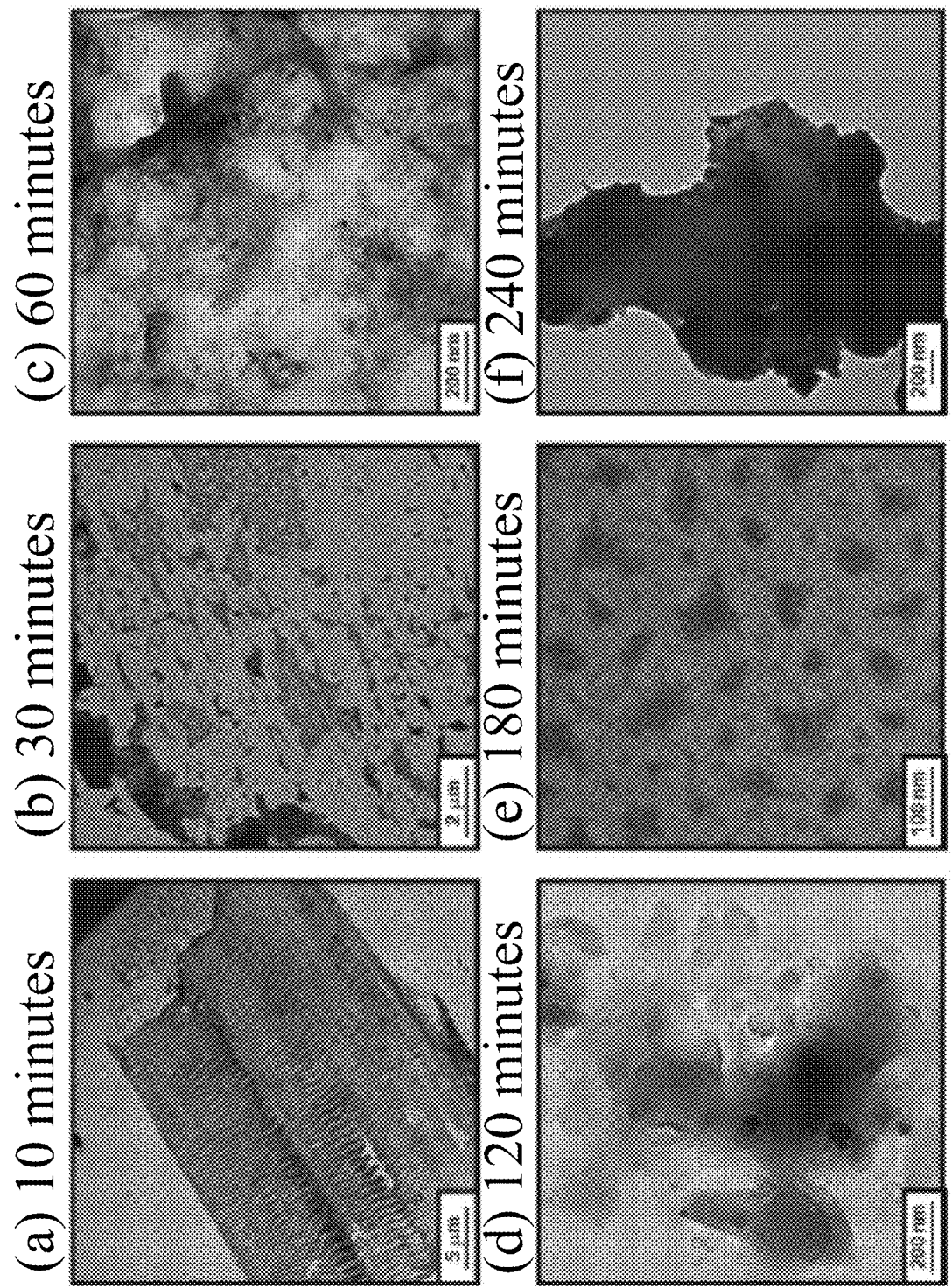
FIG. 9 shows the TEM images of the time-course formation of GNS/Alg-NGs by heating sodium alginate at 270° C. for 10 to 240 min (a)-(f).
Figure 10:
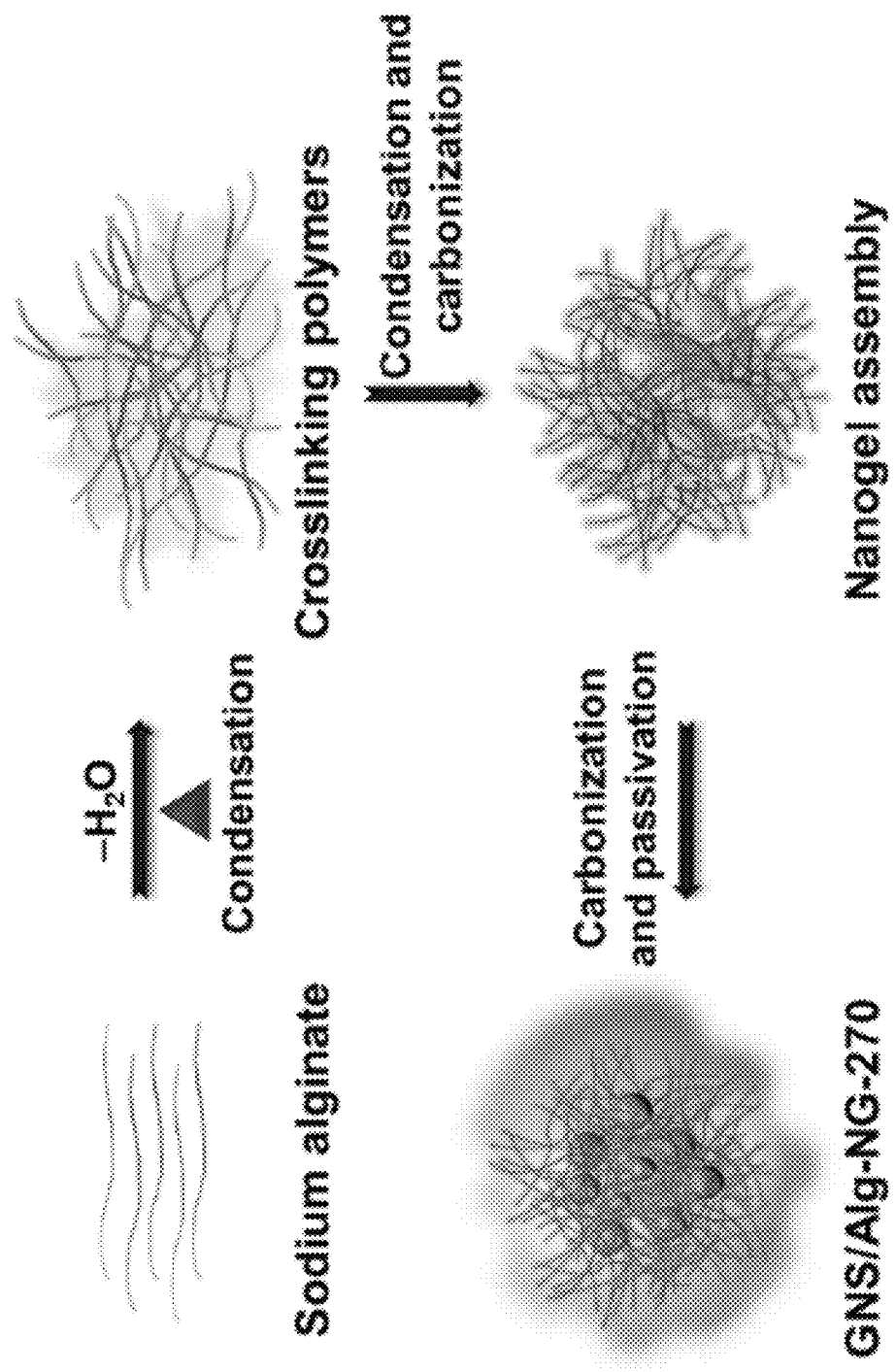
FIG. 10 shows the proposed mechanism of the formation of GNS/Alg-NGs-270.

Time course TEM images of sodium alginate heated at 270° C. showed that a gel-like structure is formed within 10 min heating (FIG. 9). Condensation of the hydroxyl and carboxylic groups of alginate resulted in cross-linking to form supramolecular-like large structures with micrometer sizes. The as-formed supramolecular structures were then fragmented into smaller particles as a result of pyrolysis at the initial stages of carbonization. Further carbonization led to the formation of amorphous carbon clusters upon heating from 30 min to 1 h, whereupon partially carbonized alginate polymeric chains or their fragment molecules constituted the NGs, as illustrated in FIG. 10. In contrast, large carbon residues formed from sodium alginate after heating for 4 h due to a higher degree of carbonization, which resulted in poor aqueous dispersibility. Therefore, a heating time of 3 h was optimal in order to preserve functional groups of sodium alginate and to achieve maximum aqueous dispersibility for bio-applications.

Figure 11A:
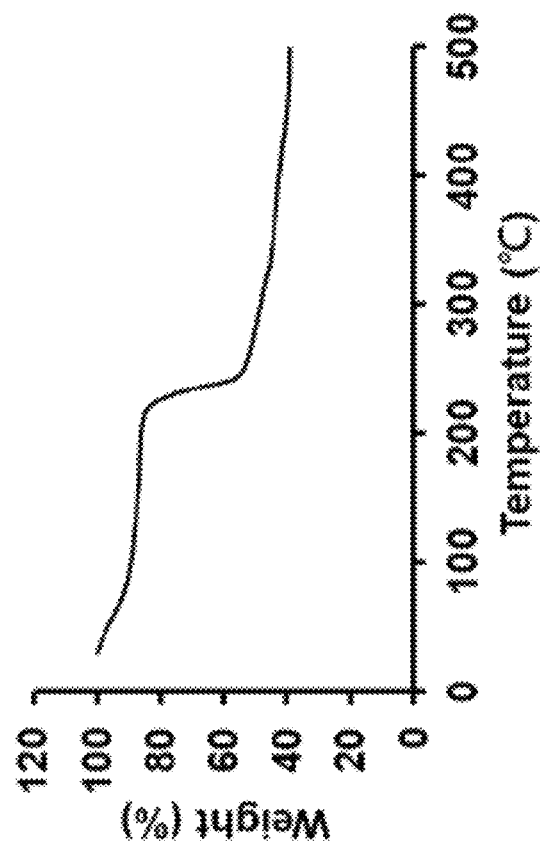
FIGS. 11A to 11C show the results of thermogravimetric analysis (TGA) and differential scanning calorimetry (DSC) of sodium alginate.
Figure 11B:
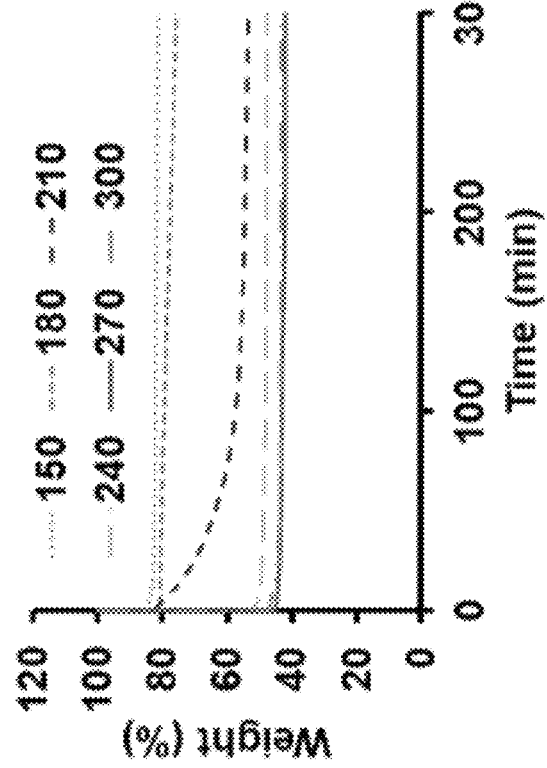
Figure 11C:
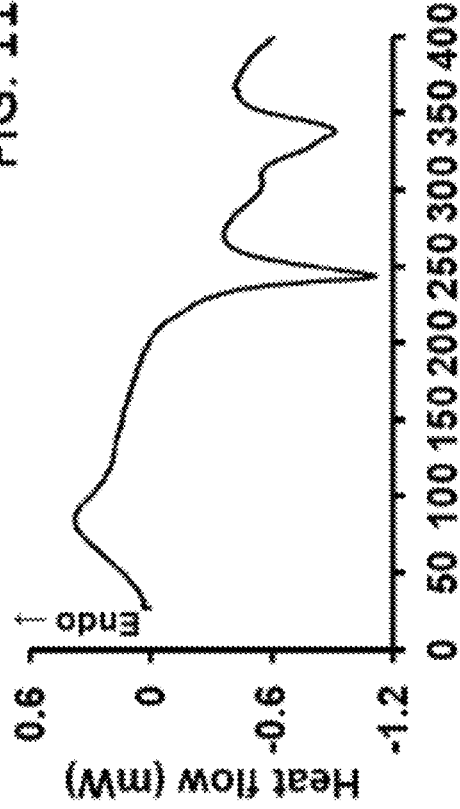

It has been found that, during heating, sodium alginate dehydrates and decomposes to $CO_2$ in three steps: water loss, the formation of a carbonaceous residue, and then $Na_2CO_3$. The thermogravimetric analysis (TGA) of time-course weight loss at constant temperatures (150° C. to 300° C.) for 3 h in the preheated analyzer was consistent with this finding (FIG. 11A). Heating at 150° C. and 180° C. resulted in less than 20% weight loss, due to the loss of water molecules. The weight losses at 210° C., 240° C., 270° C., and 300° C. were about 55% and indicated an increasing trend, suggesting a higher degree of dehydration and thermal decomposition with temperature, despite the melting point of sodium alginate being much higher (>300° C.). Temperature-dependent TGA showed that sodium alginate starts to decompose from 210° C. (FIG. 11B). Under the air atmosphere, dehydration of sodium alginate occurs at about 60° C. to about 210° C., and decomposition at about 210° C. to about 230° C. The differential scanning calorimetry (DSC) curve of the sodium alginate showed a broad endothermic band at 70° C. to 125° C. (FIG. 11C), which was attributed to water loss and the formation of cross-linking polymers by a condensation reaction. The exothermic peak at 240° C. might be a result of the initial stage of decomposition, followed by slight oxidation of carbon atoms, as well as carbonization processes leading to the formation of embedded carbon nanosheets. Some polymer-like alginate and/or its fragment polymers remained on the surfaces of the as-formed GNS/Alg-NGs, thereby conferring specific functional properties and bioactivity.

Example 3: Formation of the Phenolic Polysaccharide

Figure 12:
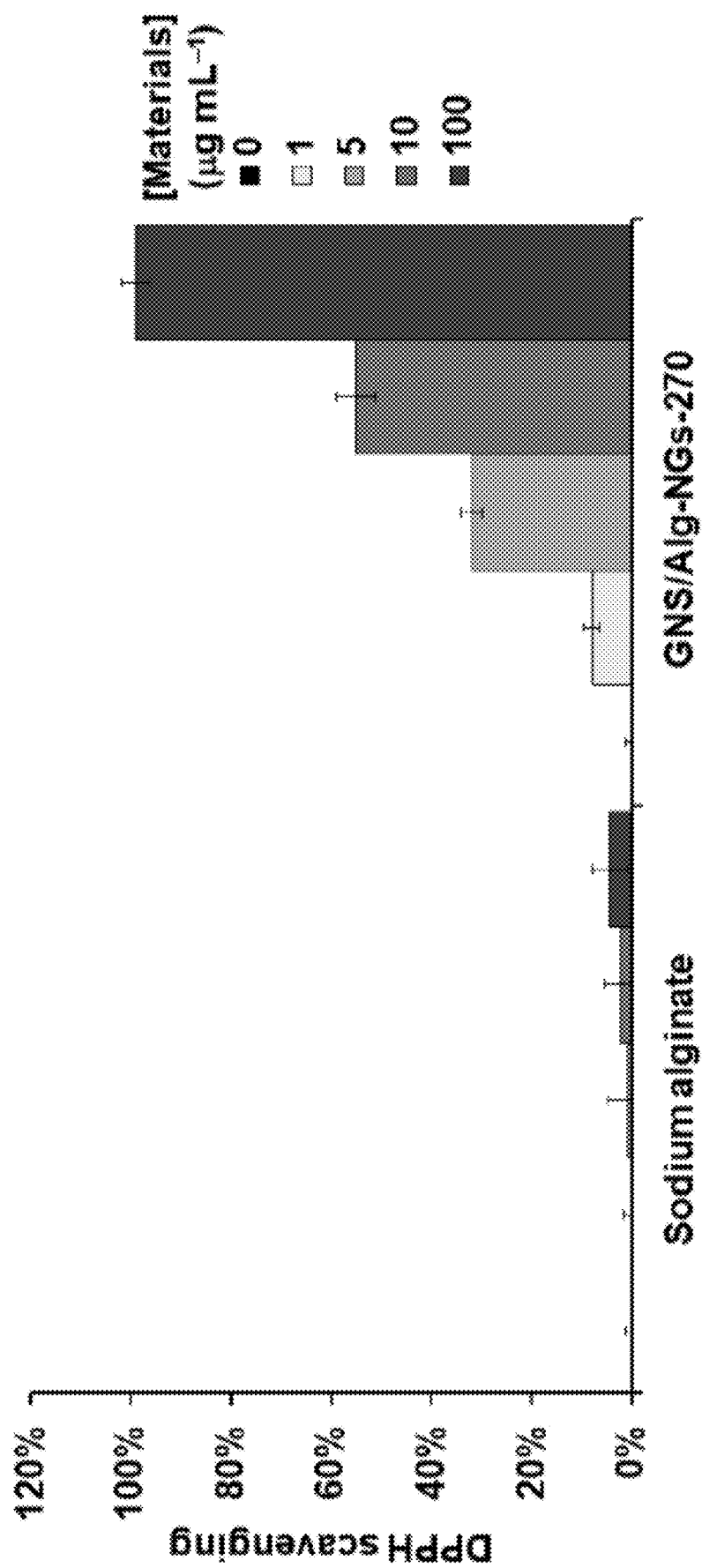
FIG. 12 shows the 2,2-diphenyl-1-picrylhydrazyl (DPPH) scavenging activity of sodium alginate and GNS/Alg-NGs-270.

It was observed that the GNS/Alg-NGs-270 showed an obvious FT-IR peak at 1330 cm⁻¹ (FIG. 8), assigned to the phenol group, which had potent antioxidant activities. To further characterize the presence of polyphenolic functional groups in the GNS/Alg-NGs, the 2,2-diphenyl-1-picrylhydrazyl (DPPH) assay, Folin-Ciocalteu assay, cyclic voltammetry (CV), and nuclear magnetic resonance (NMR) spectroscopy were conducted. The DPPH assay revealed that GNS/Alg-NGs-270 (100 μg/mL) had a superior free radical scavenging ability, about 35-fold higher than that of free sodium alginate, as shown in FIG. 12, and was supportive of the presence of polyphenolic structures. Additionally, the graphene-like nanosheet structures facilitated fast electron transfer and promoted redox reactions on the surface of GNS/Alg-NGs-270.

Next, the total amount of phenols in the GNS/Alg-NGs-270 was quantified by the Folin-Ciocalteu reagent, a mixture of phosphomolybdate and phosphotungstate, so as to evaluate their antioxidant activities. The determined reducing ability of the GNS/Alg-NGs-270 (100 μg/mL) was equivalent to 6.1 μg/mL quercetin (n=5), indicating the formation of phenolic polysaccharides. Conversely, sodium alginate (100 μg/mL) exhibited insignificant reducing ability in Folin-Ciocalteu assay. The cyclic voltammetry of GNS/Alg-NGs-270 in phosphate-buffered saline (PBS) on a glassy carbon electrode (GCE) surface further showed an oxidation peak at 0.8 V, which was consistent with the reports on oxidation of phenol groups.

Figure 13A:
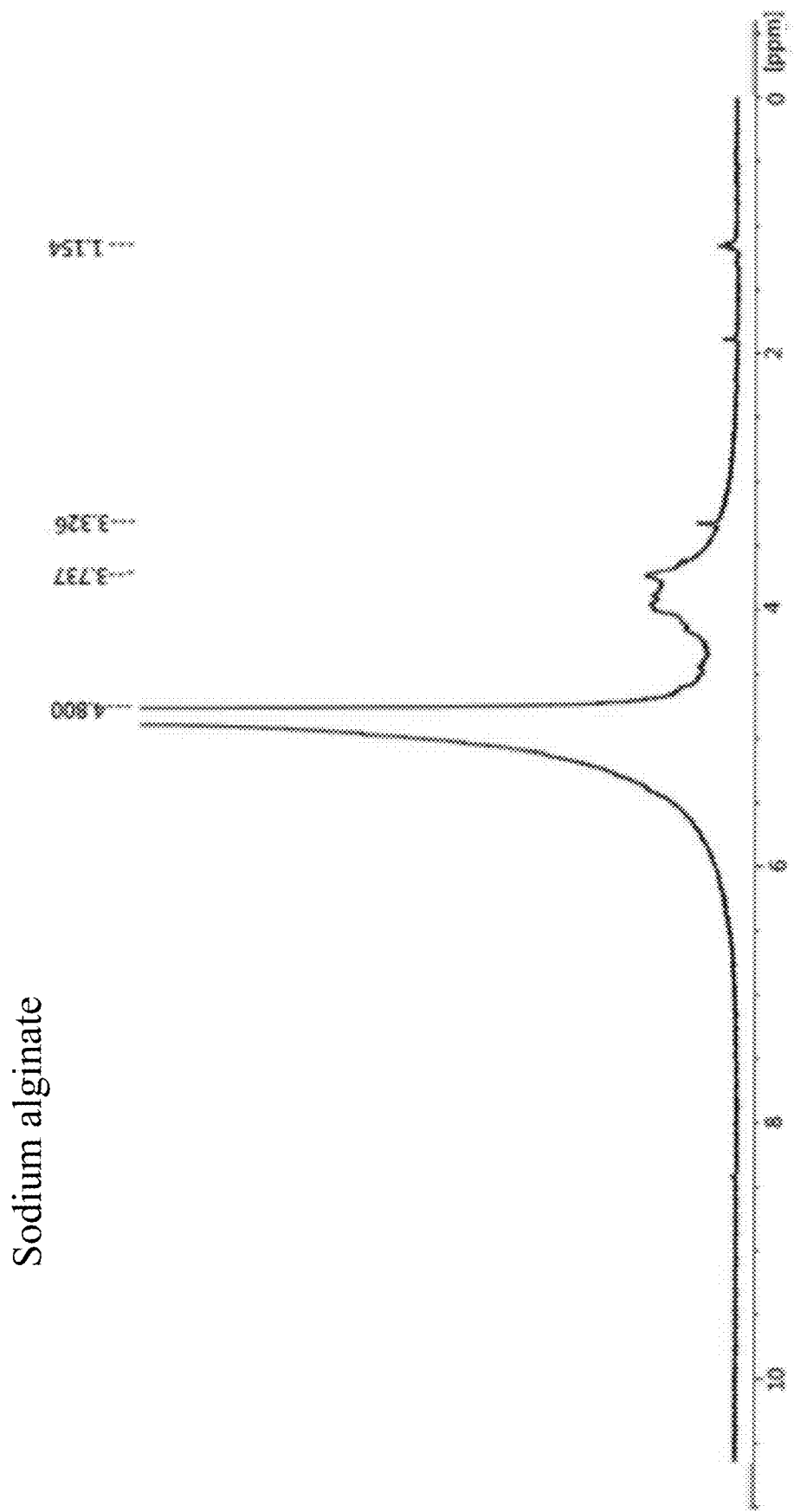
FIGS. 13A to 13C show the $^1$H-nuclear magnetic resonance (NMR) spectra of sodium alginate (FIG. 13A) and GNS/Alg-NGs-270 (FIGS. 13B and 13C) at the concentration of 50 mg/mL in deuterated water ($D_2O$) at 298 K.
Figure 13B:
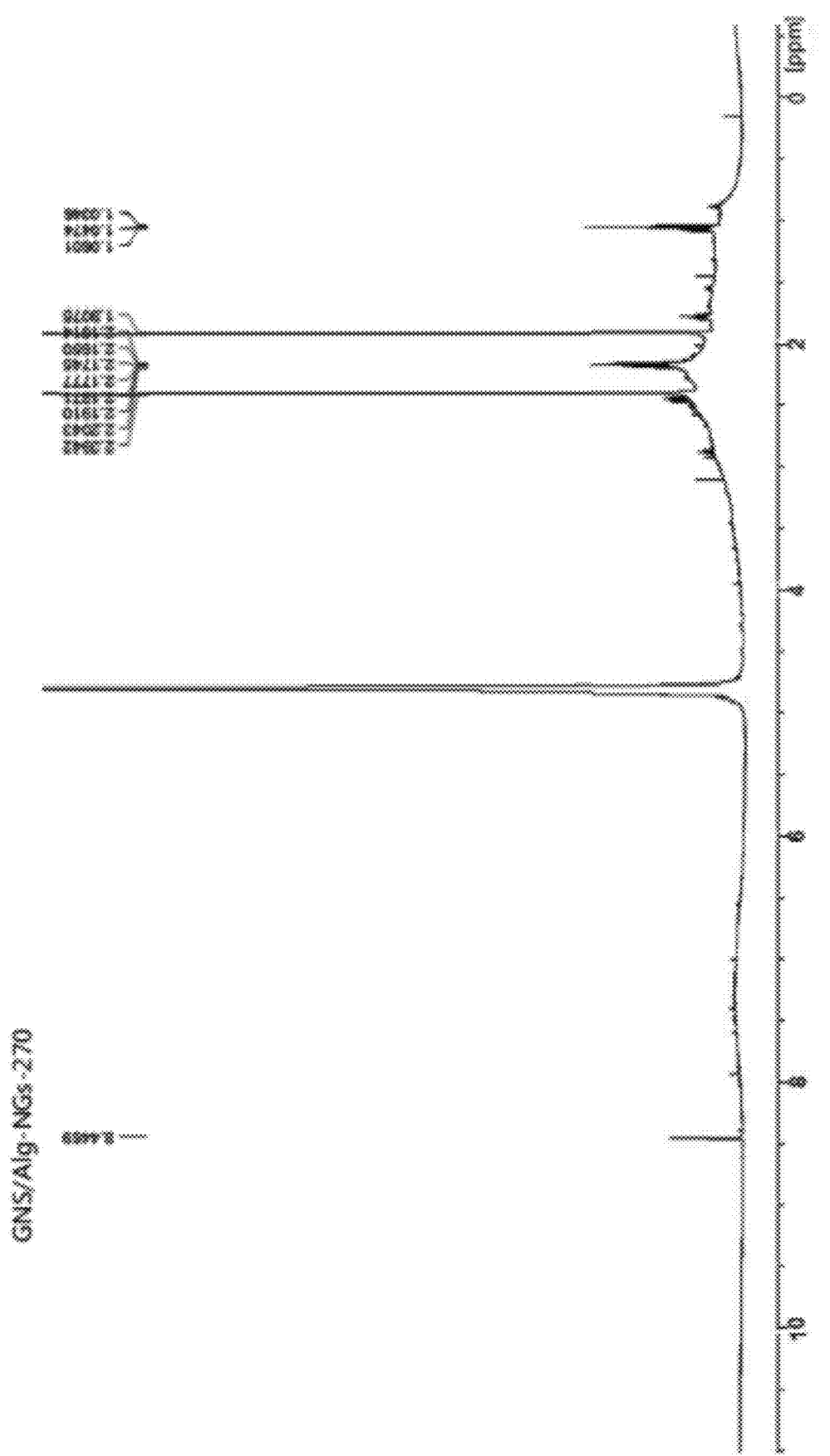
Figure 13C:
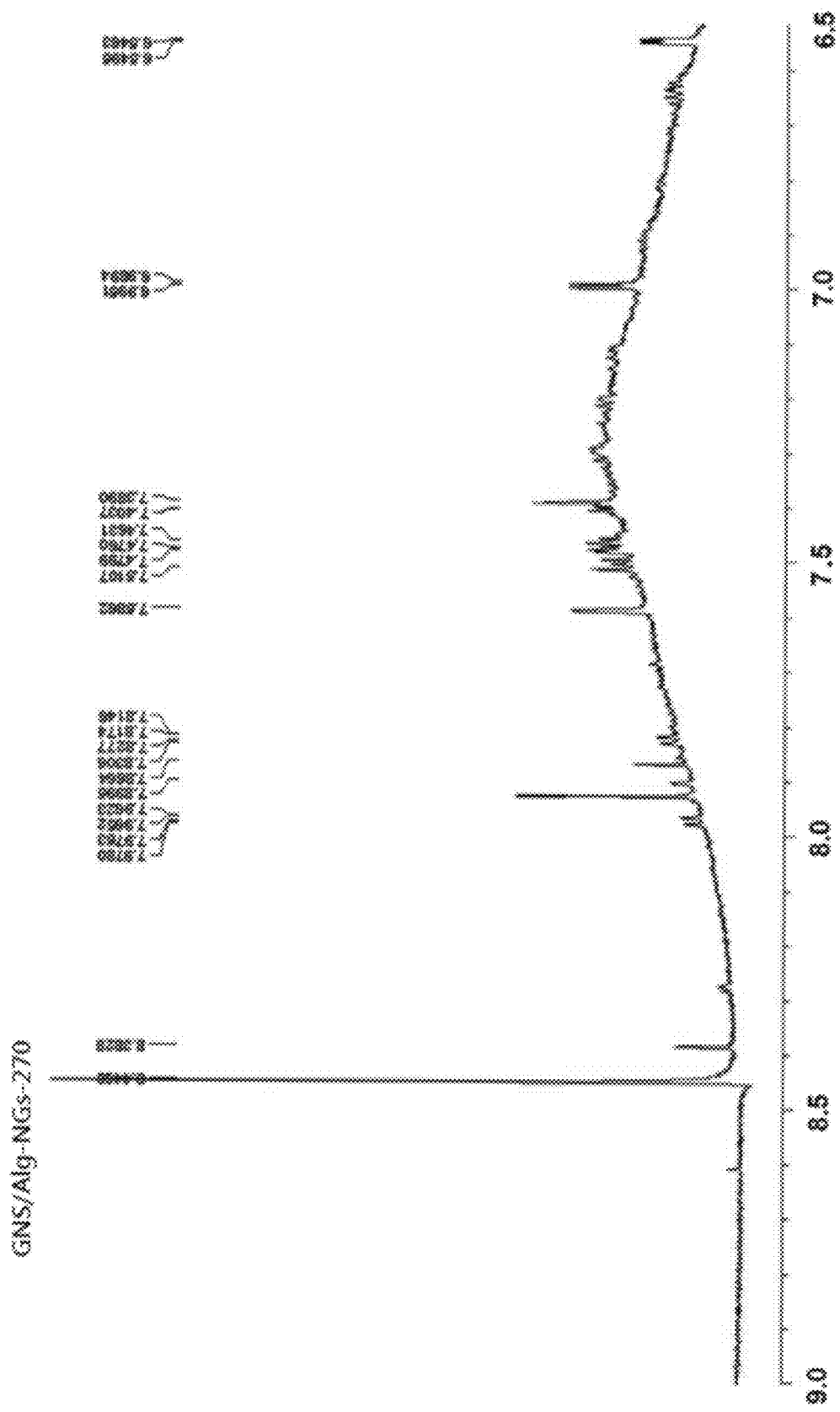

High-resolution $^1$H-NMR spectroscopy was then used for the confirmation of phenolic groups in complicated samples, such as the complex mixture of polyphenol molecules. GNS/Alg-NGs-270 in deuterated water ($D_2O$) showed $sp^a$ C—H protons at 1.0 ppm to 3.0 ppm. There were also a sharp band at 8.4 ppm and broadband with multiple peaks at 6.5 ppm to 9.0 ppm, suggesting the phenol groups on GNS/Alg-NGs-270 engaged in proton exchange between inter-/intra-molecular —OH and —OH and —COOH groups at 298 K (FIGS. 13A to 13C). The FT-IR spectrum and $^1$H NMR spectroscopy of GNS/Alg-NGs-270 showed the formation of phenol groups from the dry heating process of sodium alginate (polysaccharides).

In addition, the results from DPPH and Folin-Ciocalteu assays showed that GNS/Alg-NGs-240 and GNS/Alg-NGs-270 possessed stronger antioxidant ability than other NGs, supporting that more polyphenolic and phenolic acid structures formed during the heating of sodium alginate at 270° C. (FIGS. 14A and 14B).

Example 4: Cytotoxicity and Biocompatibility of GNS/Alg-NGs

Figure 15A:
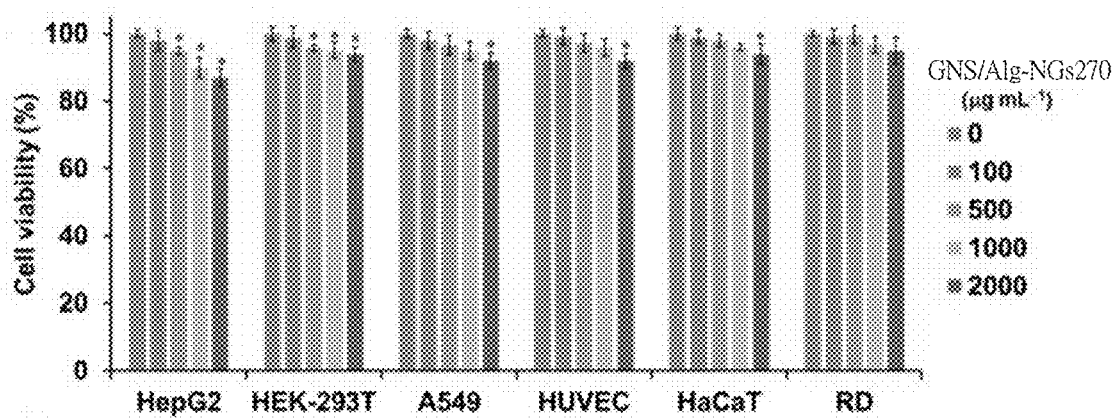
FIGS. 15A and 15B sequentially show the bar diagrams for cell viability of ten mammalian live cells.
Figure 15B:
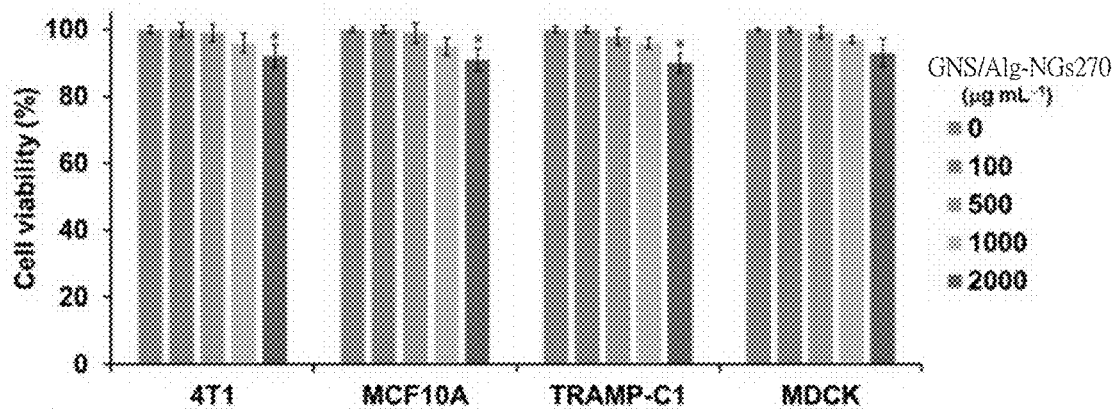
Figure 15C:
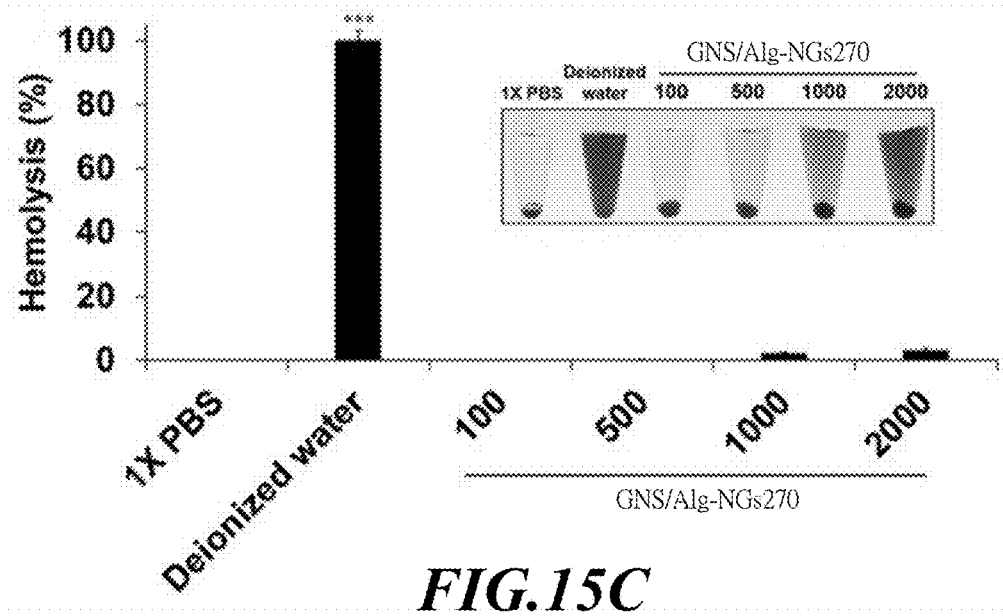
FIG. 15C shows the results of a hemolysis assay to verify the biocompatibility of GNSAlg-NGs (*$p<0.05$, ***$p<0.001$, n=3).

The cell cytotoxic and hemolytic effects of GNS/Alg-NGs-270 toward ten mammalian cell lines and red blood cells (RBCs) were evaluated in vitro. Specifically, the cytotoxicity of GNS/Alg-NGs-270 toward different mammalian cells at concentration 0 μg/mL, 100 μg/mL, 500 μg/mL, 1000 μg/mL, 2000 μg/mL, was evaluated by the PrestoBlue cell viability assay, respectively. FIG. 15A showed HaCaT, HUVEC, HEK-293T, RD, HepG2 and A549 cells were incubated for 72 h. FIG. 15B showed 4T1, TRAMP-C1, MDCK, MCF10A cells were incubated for 72 h. They showed higher than 90% cell viability for all cells incubated in GNS/Alg-NGs-270 at the concentration lower than 1000 μg/mL of and higher than 85% cell viability for all cells incubated in GNS/Alg-NGs-270 at the concentration lower than 2000 μg/mL, indicating that GNS/Alg-NGs-270 displayed negligible cytotoxicity toward mammalian cells. Furthermore, in vitro hemolysis assay with 1×PBS and deionized water were used as negative and positive controls, respectively, and the results (FIG. 15C) showed no significant hemolysis in RBCs after incubation with GNS/Alg-NGs-270 (0.1 mg/mL to 2.0 mg/mL), indicating that GNS/Alg-NGs-270 was a safe injectable anti-metastasis drug.

Example 5: Anti-Metastasis Activity of GNS/Alg-NGs

Figure 16A:
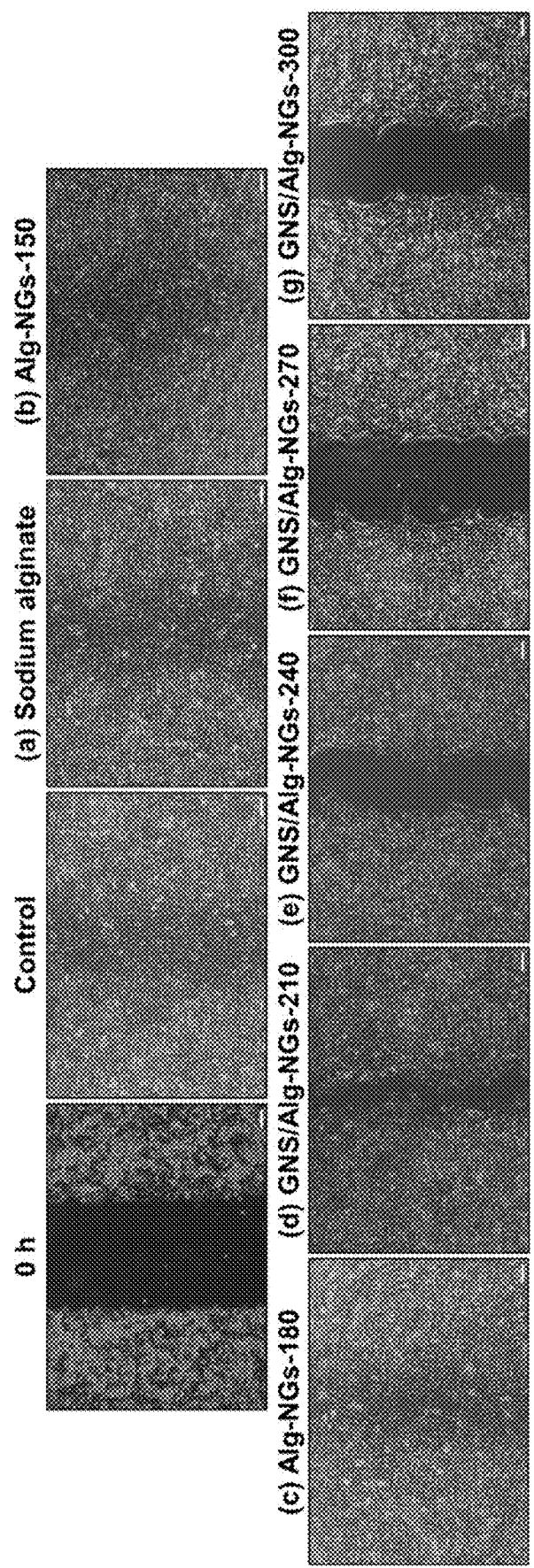
FIG. 16A sequentially shows the experiment result pictures of inhibition effect of 0 hours group, the control group, (a) sodium alginate, (b-g) Alg-NGs or GNS/Alg-NGs treated at different temperatures on cancer cell migration.
Figure 16B:
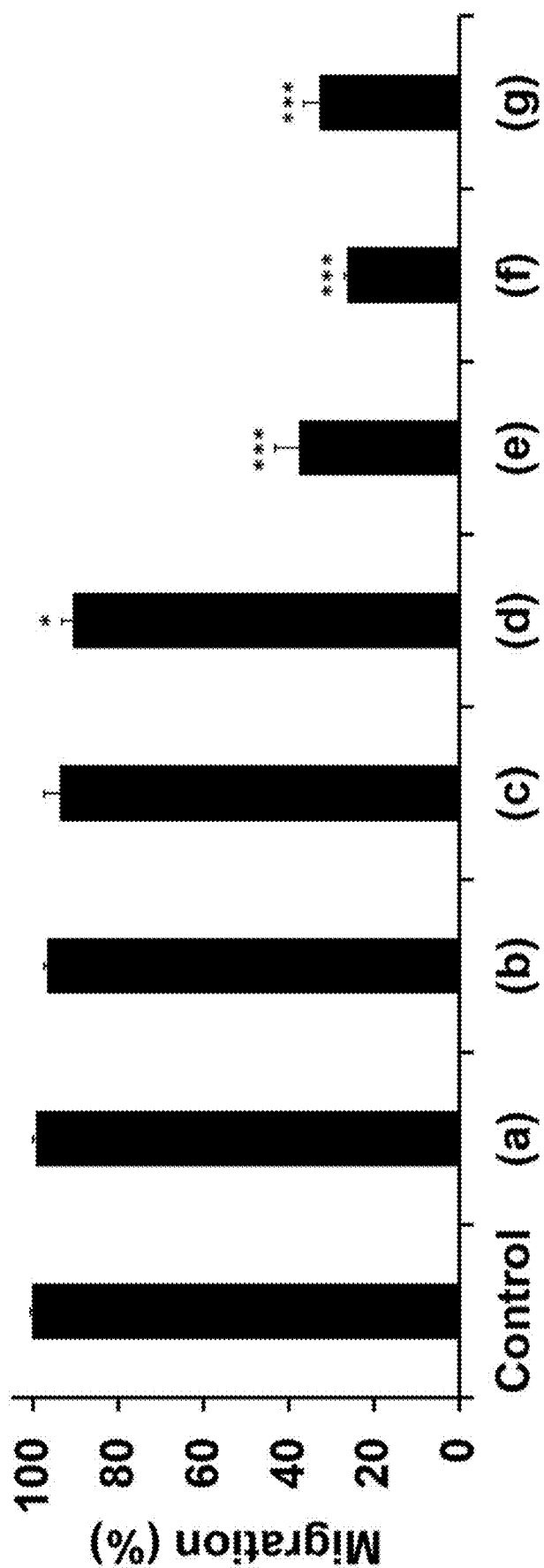
FIG. 16B shows scale bars of cell migration rate of control group, (a) sodium alginate, (b-g) Alg-NGs or GNS/Alg-NGs treated at different temperatures (*$p<0.05$, ***$p<0.001$, n=3).

As shown in FIG. 16A, a wound healing assay was used to evaluate the migration ability of cancer cells. At the beginning of the experiment (0 hours), the black gap in the middle was a cell-free area. After 12 hours of incubation, in the control group incubated in RPMI medium, cancer cells filled the gaps. However, the groups incubated in GNS/Alg-NGs-240, GNS/Alg-NGs-270 or GNS/Alg-NGs-300 still maintained significant gaps. As shown in FIG. 16B, the migration rates of cancer cells in the GNS/Alg-NGs-240, GNS/Alg-NGs-270 and GNS/Alg-NGs-300 groups were 37%, 26%, and 33%, respectively. The significance decrease of migration rate than other groups indicates the inhibition of migration of cancer cells, thus provides a very good anti-metastasis activity. In particular, GNS/Alg-NGs-270 has excellent inhibition of cancer cell migration rate, which is speculated to be related to its excellent performance in antioxidant capacity.

Figure 17A:
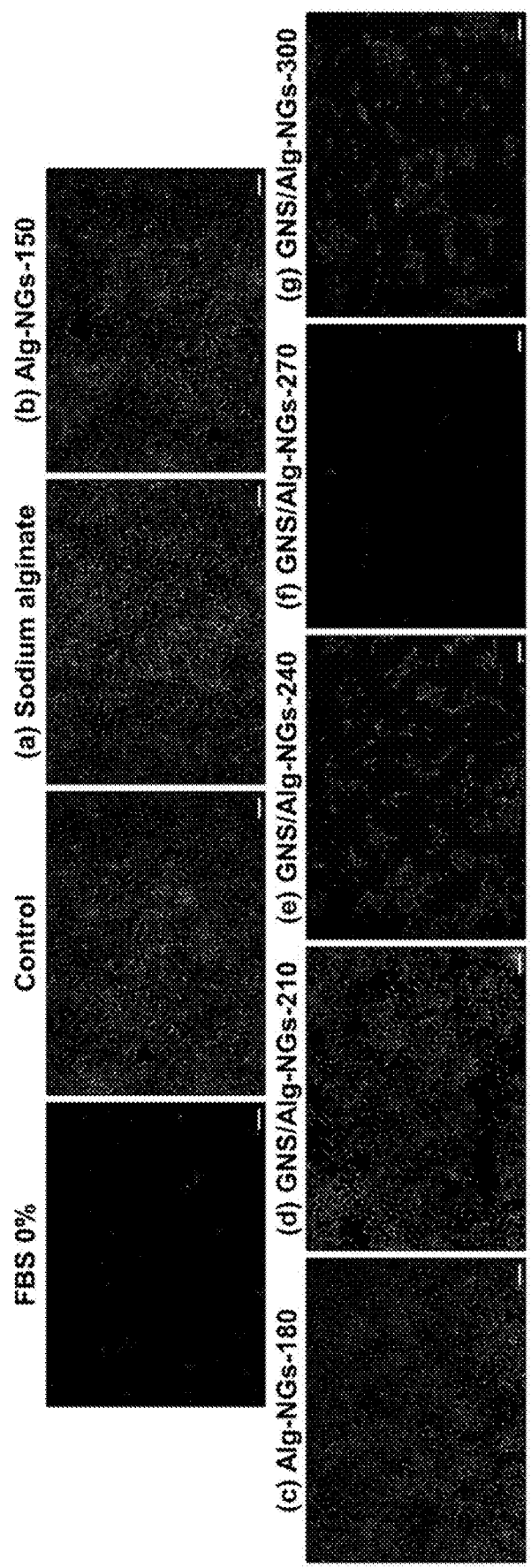
FIG. 17A sequentially shows the experiment result pictures of inhibition effect of the PBS 0% group, control group, (a) sodium alginate, (b-g) Alg-NGs or GNS/Alg-NGs treated at different temperatures on cancer cell invasion.

Next, metastatic ability was assessed using a cancer cell invasion assay. 4T1 cells in the upper chamber with a layer of Matrigel have the ability to decompose Matrigel due to the high concentration of FBS in the lower chamber. Thus, 4T1 cells invade to the lower chamber. The cells in the lower chamber could be stained with Hoechst stain and observed under a fluorescence microscope. As shown in FIG. 17A, when the culture medium in the lower chamber contained 0% FBS (negative control group), 4T1 cells did not have the ability to invade to the lower chamber. When the culture medium in the lower chamber contained 10% FBS ((positive) control group), 4T1 cells invaded downward and were observed by fluorescence microscopy due to staining.

Figure 17B:
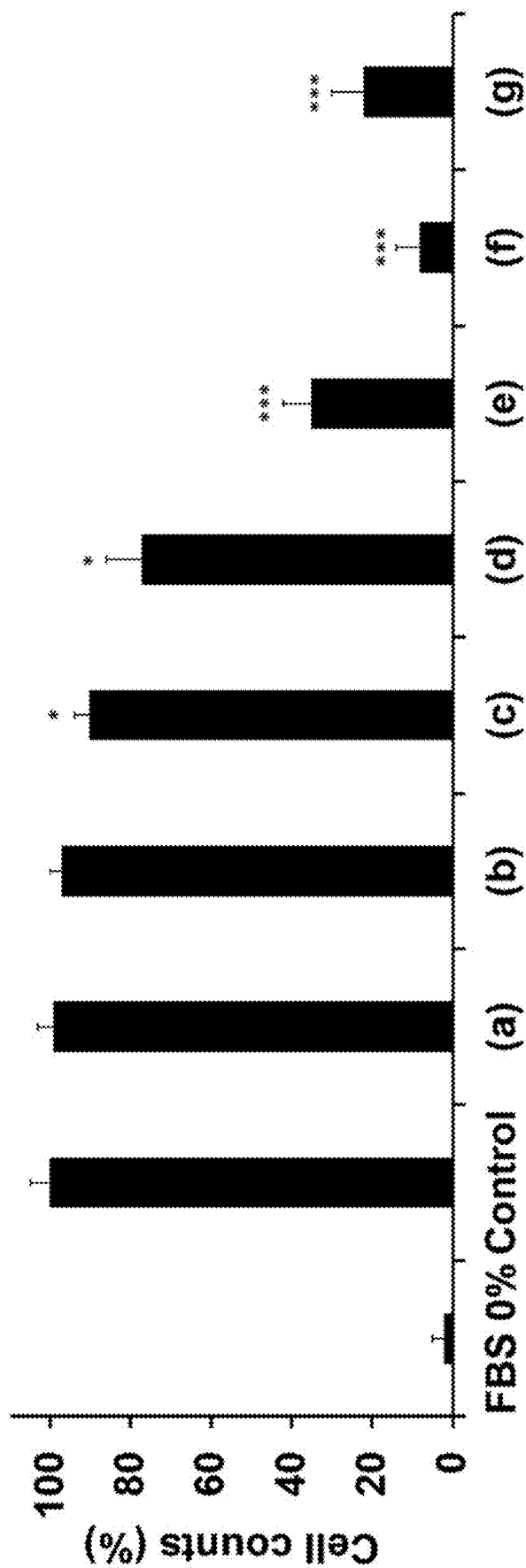
FIG. 17B shows scale bars of cell counts in the groups of FIG. 17B (*$p<0.05$, ***$p<0.001$, n=3).

In addition, referring to FIG. 17B at the same time, the culture medium in the upper chamber was alginate, Alg-NGs-150, Alg-NGs-180, GNS/Alg-NGs-210, GNS/Alg-NGs-240, GNS/Alg-NGs-270 or GNS/Alg-NGs-300 in each group respectively. In the staining of invasive cells in the lower chamber, it is found that only 35%, 8% and 22% of the cells invaded into the lower chamber in GNS/Alg-NGs-240, GNS/Alg-NGs-270 or GNS/Alg-NGs-300 groups, respectively, thus no obvious blue fluorescence was observed. Compared with the control group, the number of invasive cells was significantly reduced, which represented the ability to inhibit cell invasion, especially GNS/Alg-NGs-270 had a higher activity on the inhibition of cell invasion.

Figure 18A:
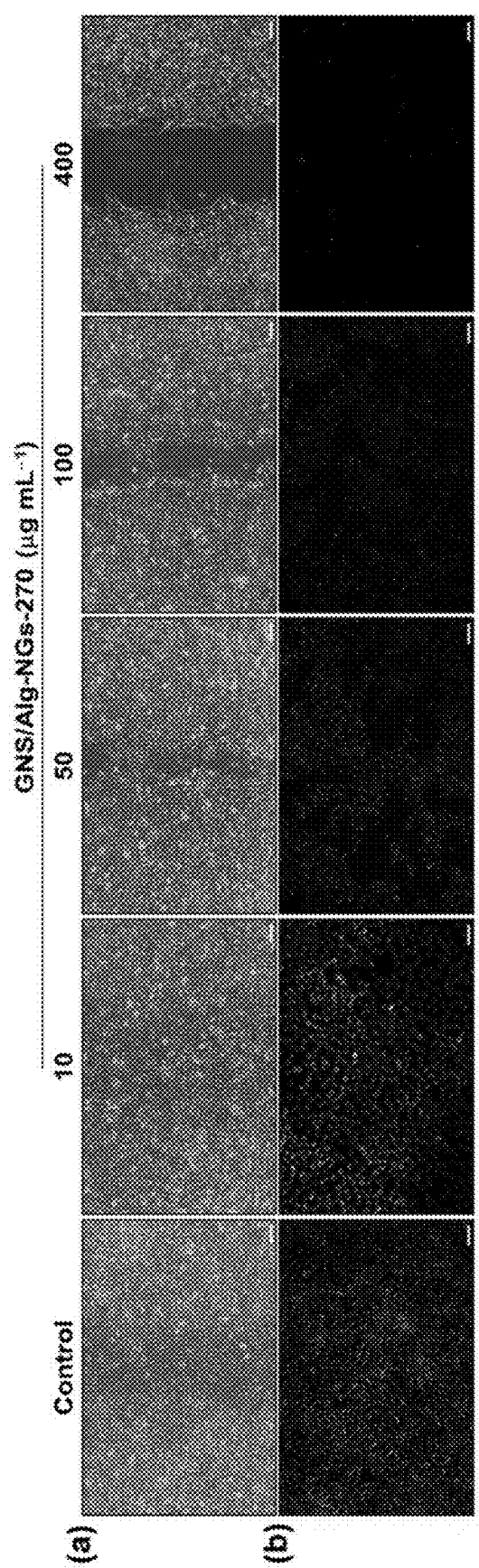
FIG. 18A (a) sequentially shows the experiment result pictures of inhibition effect of control group, GNS/Alg-NGs-270 at 10 μg/mL, 50 μg/mL, 100 μg/mL, and 400 μg/mL on cancer cell migration.
Figure 18B:
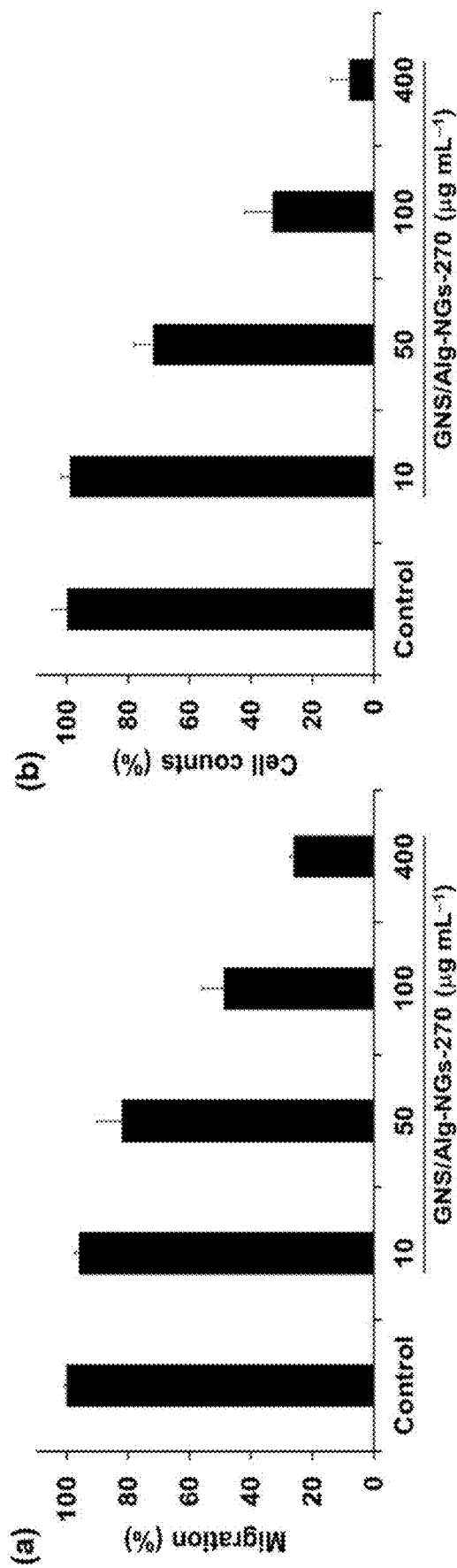
FIG. 18B (b) shows scale bars of cell counts in the groups of FIG. 18A (b) (*p<0.05, ***p<0.001, n=3).

Furthermore, FIG. 18A (a) and FIG. 18B (a) showed the dose-dependence of anti-migration activity. GNS/Alg-NGs-270 was tested at concentrations of 10 μg/mL, 50 μg/mL, 100 μg/mL, 400 μg/mL culture medium after culturing for 12 hours, it was observed that the higher concentration of GNS/Alg-NGs-270 inhibited the migration of cancer cells, left obvious gaps, and also made the migration rate of cancer cells significantly lower than other groups. FIG. 18A (b) and FIG. 18B (b) were also observed that higher concentration of GNS/Alg-NGs-270 inhibited the invasion of cancer cells after 12 hours of incubation in the medium containing GNS/Alg-NGs-270 at the concentration of 10 μg/mL, 50 μg/mL, 100 μg/mL, and 400 μg/mL, less obvious blue fluorescence could be observed, and the number of invasive cells also decreased significantly.

Example 6: Animal Experiments on Antitumor Ability of GNS/Alg-NGs

Figure 19B:
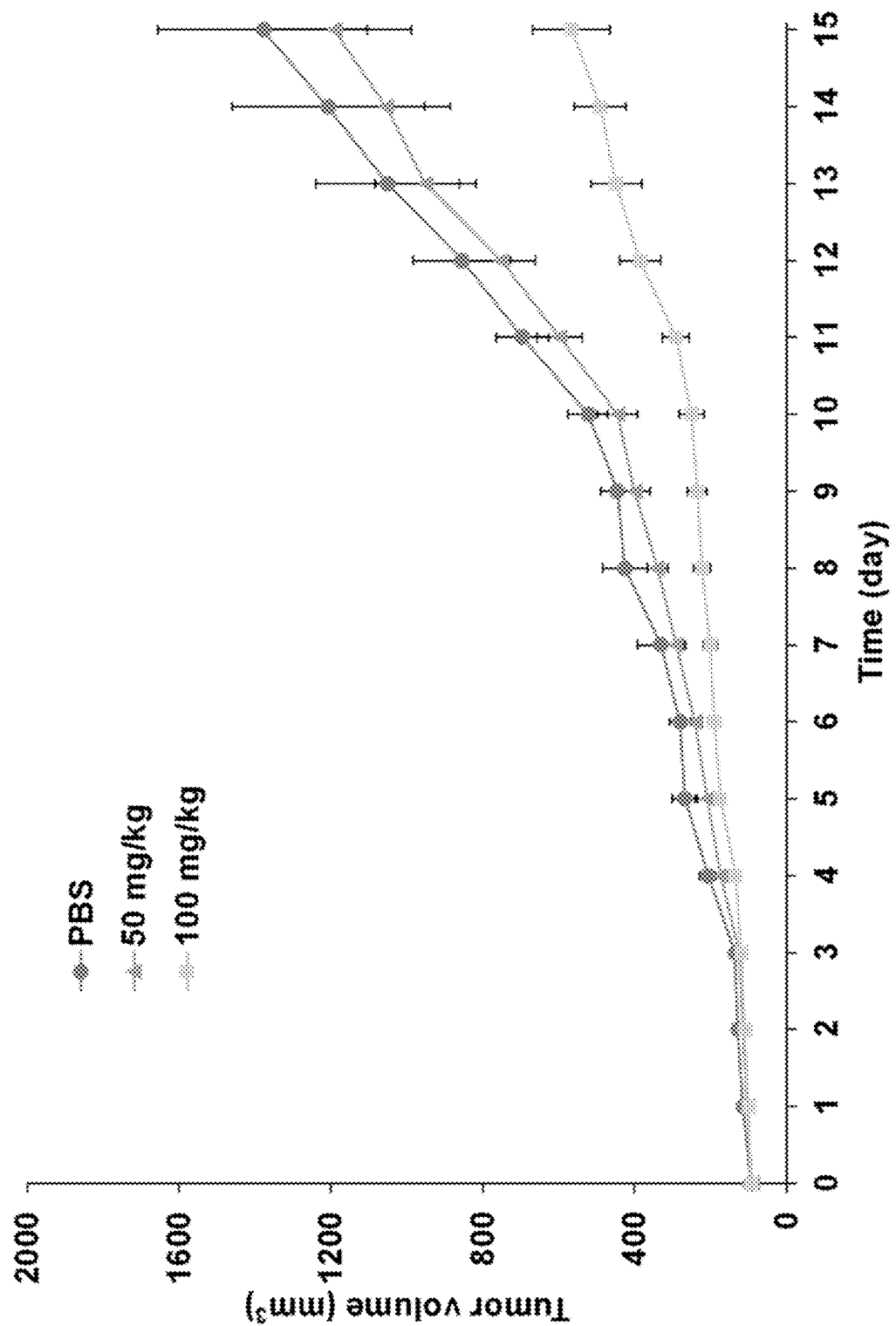
FIG. 19B shows the tumor volume curve in BALB/c mice during the administration period (PBS in the control group, 50 mg/kg GNS/Alg-NGs-270 in the low-dose group and 100 mg/kg GNS/Alg-NGs-270 in the high-dose group) of the animal experiment.
Figure 19C:
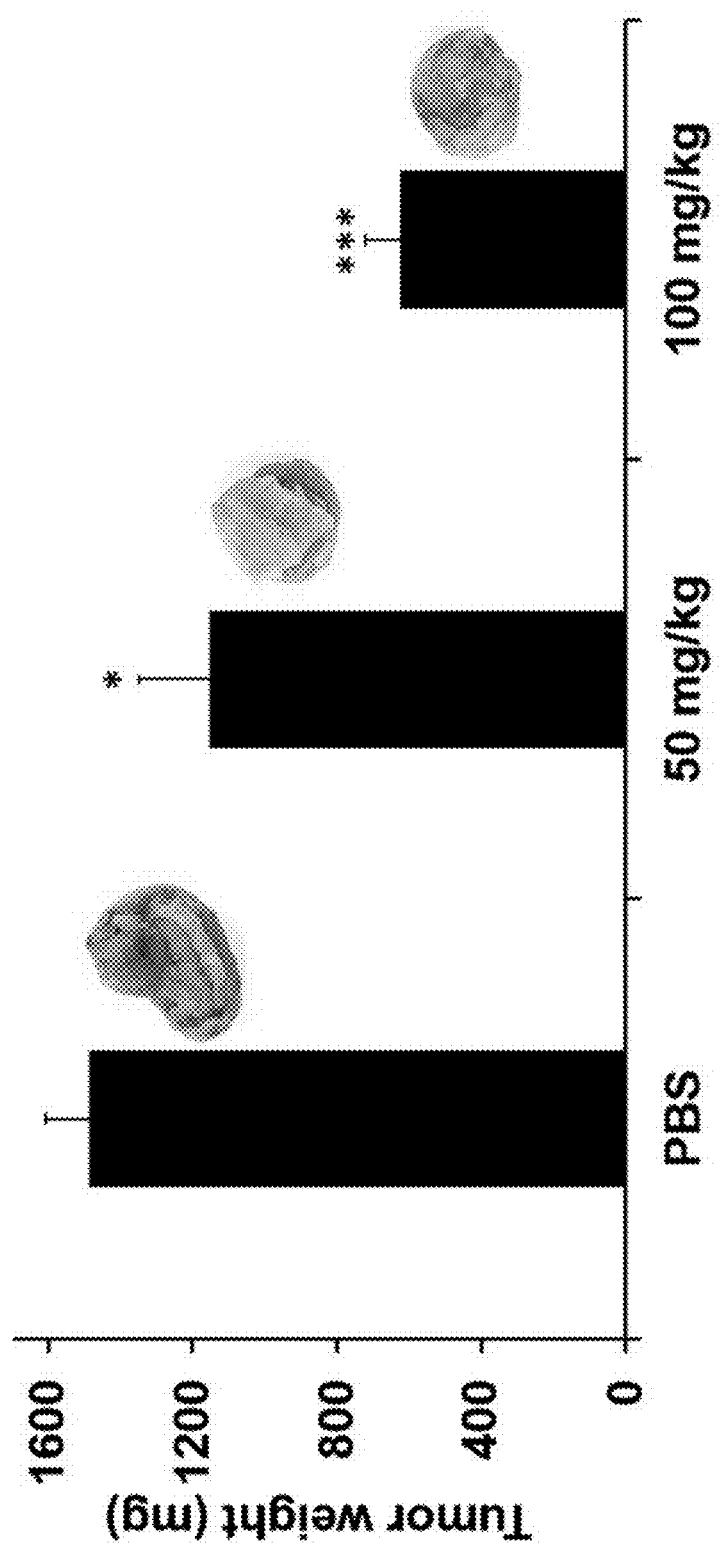
FIG. 19C is a bar diagram of tumor weights after mice sacrificed in PBS, 50 mg/kg and 100 mg/kg GNS/Alg-NGs-270 groups in animal experiments.
Figure 19D:
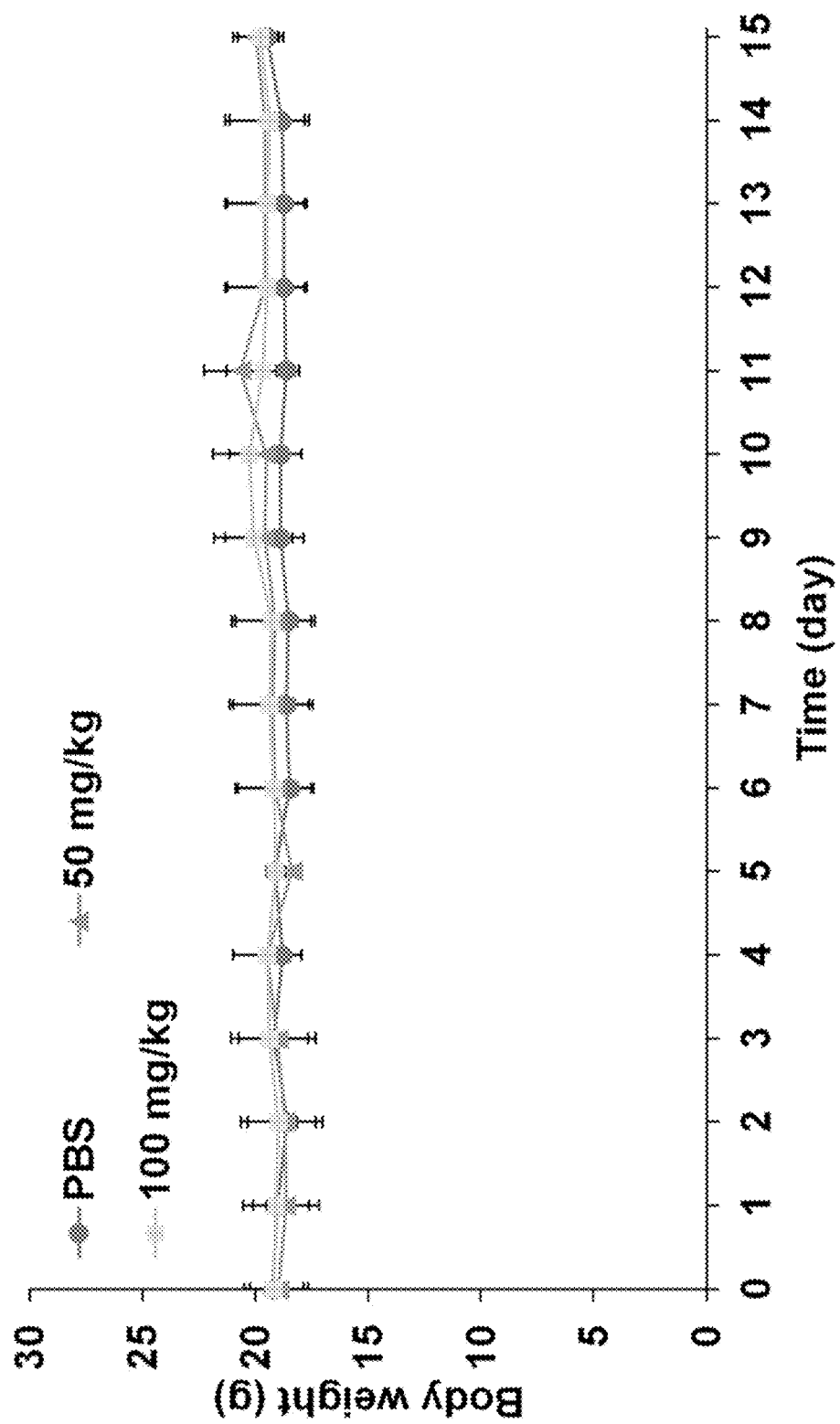
FIG. 19D is a graph showing the body weight change of mice during the administration period (PBS, 50 mg/kg and 100 mg/kg of GNS/Alg-NGs-270) of the animal experiment.
Figure 19E:
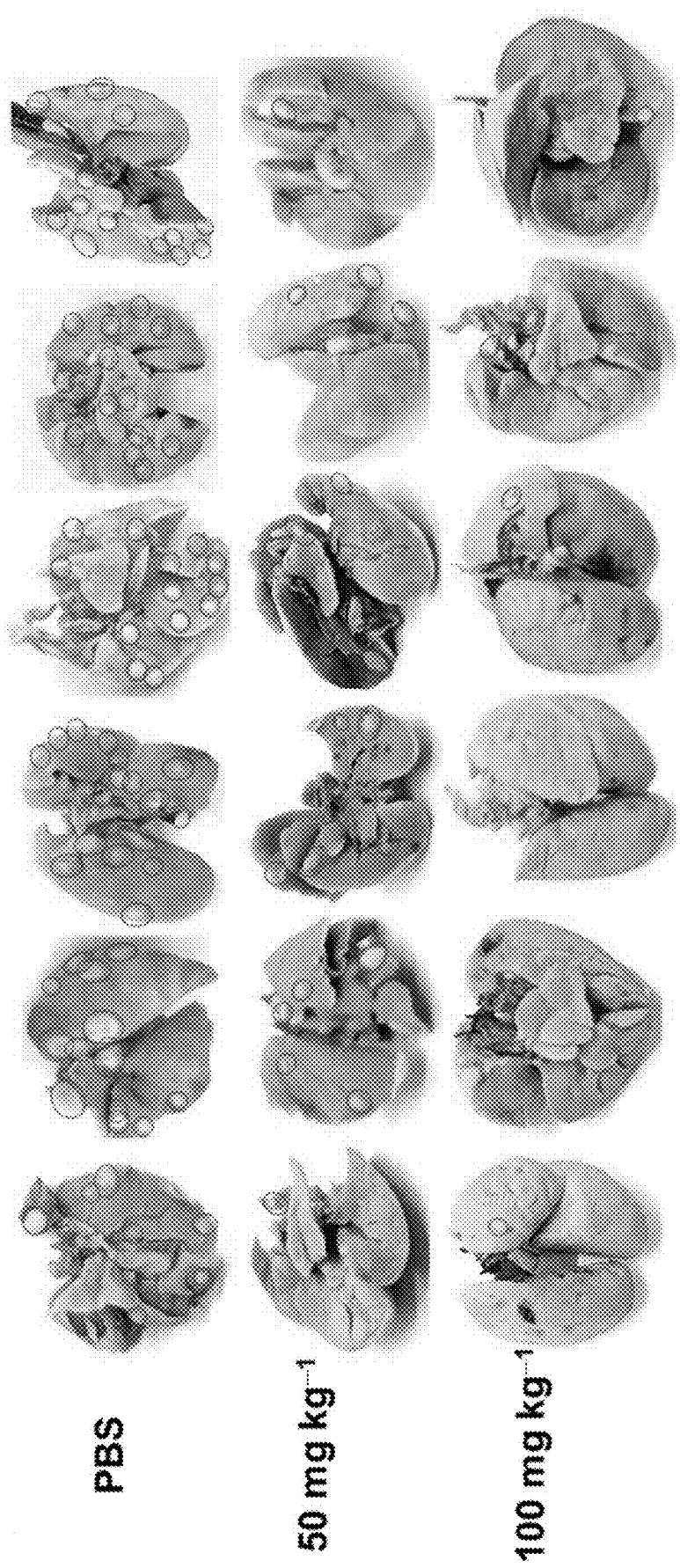
FIG. 19E is a photo of the lungs of each mouse after sacrifice in the PBS, 50 mg/kg and 100 mg/kg GNS/Alg-NGs-270 groups in the animal experiment, and the nodules are marked with a red circle.
Figure 19F:
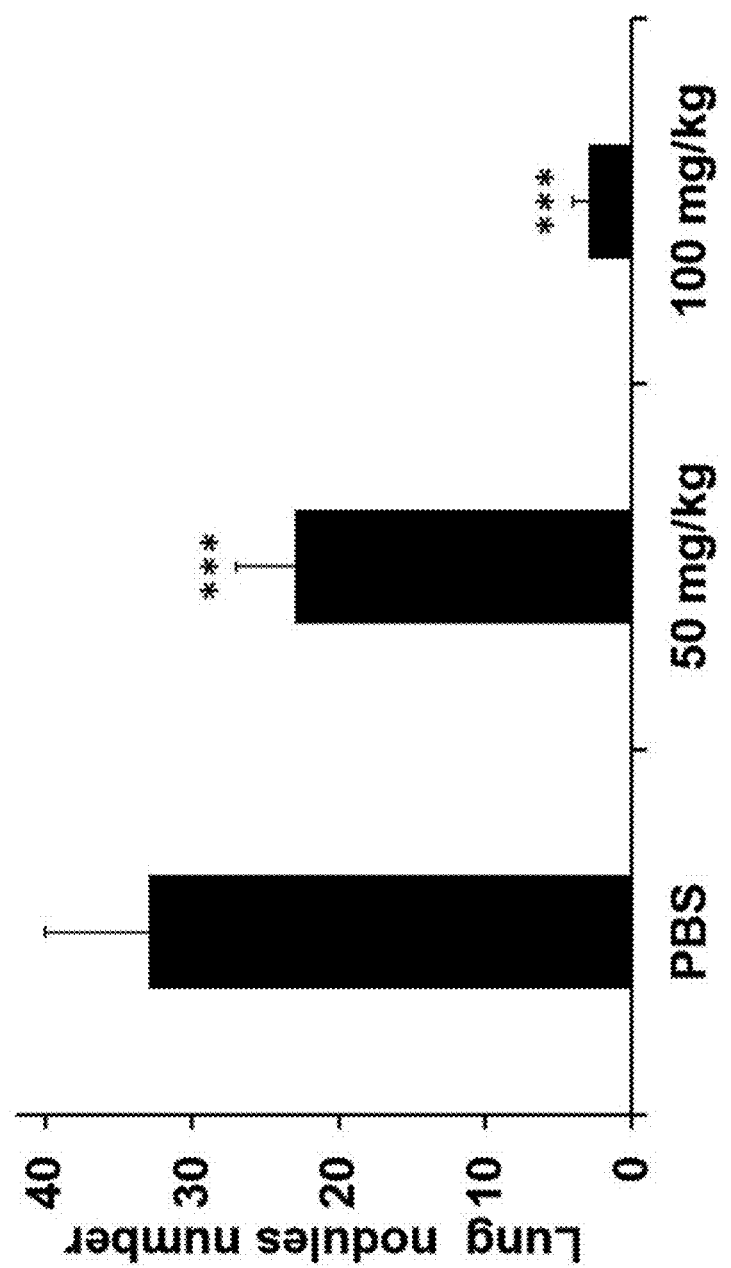
FIG. 19F and FIG. 19G are bar graphs of the lung nodules number and murine carcinosis index (MCI) of PBS, 50 mg/kg and 100 mg/kg GNS/Alg-NGs-270 groups in the animal experiment, respectively (*p<0.05, p<0.01, *p<0.001, n=6).
Figure 19G:
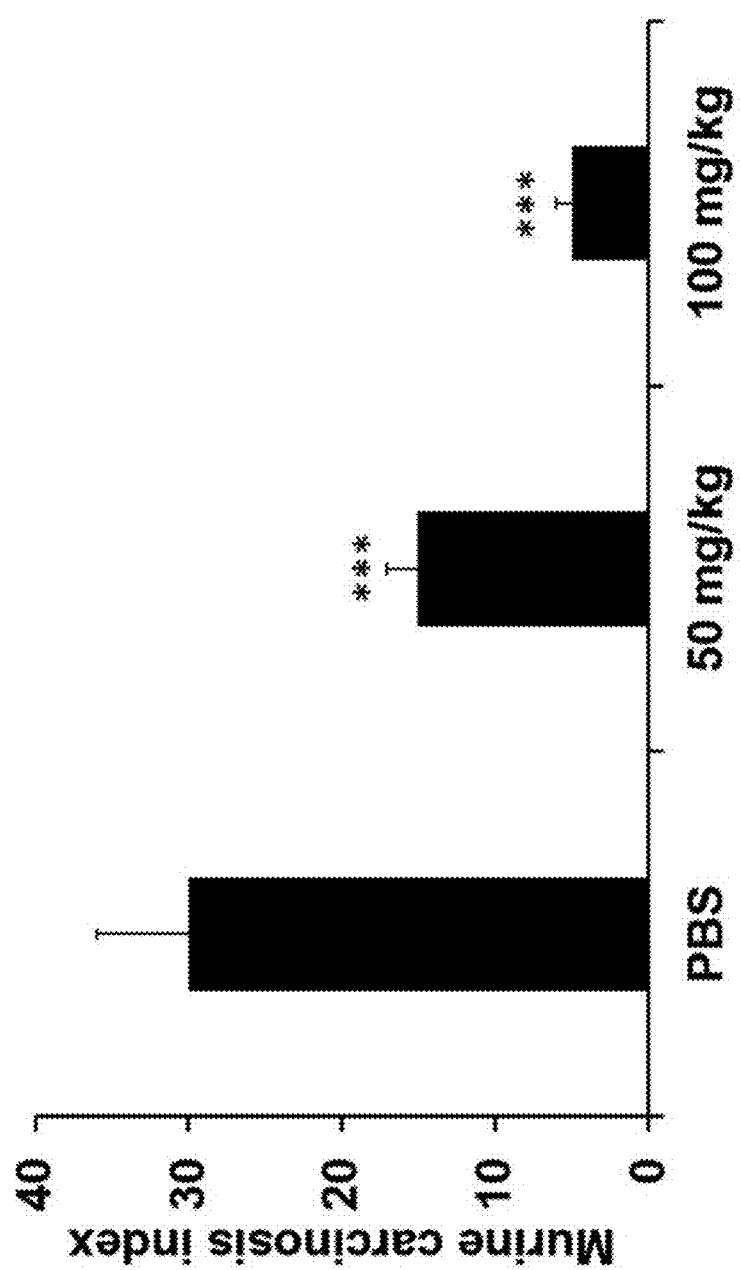

The antitumor activity of GNS/Alg-NGs-270 was tested according to the method in FIG. 19A. As shown in FIG. 19B, compared with the control group, the high-dose group had an approximately 0.23-fold reduction in tumor volume growth, indicating that tumor growth was significantly inhibited. As shown in FIG. 19C, the tumor weight after sacrifice was also consistent with that the higher dose of GNS/Alg-NGs-270 can inhibit the tumor growth more obviously. As shown in FIG. 19D, the body weight of the mice did not change much, indicating that the drug is highly biocompatible. FIG. 19E is a schematic pictures of the sacrificed mice's lungs. Since the breast cancer cells have been reported to metastasize to the lungs easily, the nodules visible on the surface of the lungs were circled, the number and the size of nodules were counted and measured, and then the parameters in Table A were used to calculate the murine carcinosis index. As shown in FIG. 19F and FIG. 19G, the mice treated with higher doses of GNS/Alg-NGs-270 significantly reduced the number of lung nodules and the murine carcinosis index compared with those treated with PBS alone. Animal experiments proved that GNS/Alg-NGs-270 effectively inhibited tumor cell metastasis.

Therefore, it can be known from the above examples that the polysaccharide carbon nanogel exhibits graphene-like structure, and its polyphenol functional group on it has good antioxidant capacity, and it also proves to have excellent anti-tumor and anti-metastasis activities, and inhibit the cancer cell migration and cancer cell invasion, and demonstrates dose-dependence. Compared with common materials with polyphenol functional groups, the polysaccharide carbon nanogel of the present invention has better water solubility, biocompatibility, stability and yield, and can be used as an ideal anti-tumor/anti-metastasis pharmaceutical composition.

The present disclosure includes embodiments in which exactly one member of the group is present in, employed in, or otherwise relevant to a given product or process. The present disclosure also includes embodiments in which more than one, or all of the group members are present in, employed in, or otherwise relevant to a given product or process.

Those skilled in the art will recognize, or be able to ascertain by using no more than routine experimentation, many equivalents to the embodiments of the present disclosure which is described herein. The scope of the present disclosure is not intending to be limited to the embodiments disclosed, but rather includes all embodiments falling within the scope of the appended claims. In addition, many modifications will be appreciated to adapt a particular instrument, situation, or material to the teachings of the present disclosure without departing from the scope thereof.

What is claimed is:

1. A pharmaceutical composition for treating tumor disease or neoplastic disorder comprising a nanogel and a pharmaceutically acceptable vehicle thereof, wherein the nanogel comprises a graphene-like nanosheet and a polysaccharide, and the graphene-like nanosheet comprises a carbonization product of at least a portion of the polysaccharide, and the graphene-like nanosheet is complexed with the polysaccharide to form a cross-linked supramolecular structure;

wherein the polysaccharide is a salt of alginic acid.

2. The pharmaceutical composition of claim 1, wherein the salt of alginic acid is selected from the group consisting of sodium alginate, calcium alginate, magnesium alginate, and any combination thereof.

3. The pharmaceutical composition of claim 1, wherein the cross-linked supramolecular structure has a functional group selected from the group consisting of hydroxyl, ester, phenol, carboxyl and any combination thereof on a surface thereof.

4. The pharmaceutical composition of claim 1, wherein the polysaccharide has a free end and a fixed end, and the fixed end of the polysaccharide is bonded to the surface of the graphene-like nanosheet.

5. The pharmaceutical composition of claim 1, wherein the nanogel has a hydrodynamic diameter ranging from 20 nm to 490 nm.

6. The pharmaceutical composition of claim 5, wherein the nanogel has a hydrodynamic diameter ranging from 40 nm to 250 nm.

7. The pharmaceutical composition of claim 1, wherein the nanogel has a zeta potential ranging from −26.5 mV to −47.5 mV.

8. The pharmaceutical composition of claim 1, wherein the nanogel is prepared by dry heating the polysaccharide to be carbonized.

9. The pharmaceutical composition of claim 1, wherein the graphene-like nanosheet has lattice planes of (100) and (112) facets.

10. A method for treating tumor disease or neoplastic disorder in a subject in need thereof, comprising administering to the subject a pharmaceutical compositions comprising a nanogel, wherein the nanogel comprises a graphene-like nanosheet and a polysaccharide, and the graphene-like nanosheet comprises a carbonization product of at least a portion of the polysaccharide, and the graphene-like nanosheet is complexed with the polysaccharide to form a cross-linked supramolecular structure;

wherein the polysaccharide is a salt of alginic acid.

11. The method of claim 10, wherein the salt of alginic acid is selected from the group consisting of sodium alginate, calcium alginate, magnesium alginate, and any combination thereof.

12. The method of claim 10, wherein the cross-linked supramolecular structure has a functional group selected from the group consisting of hydroxyl, ester, phenol, carboxyl and any combination thereof on a surface thereof.

13. The method of claim 10, wherein the polysaccharide has a free end and a fixed end, and the fixed end of the polysaccharide is bonded to the surface of the graphene-like nanosheet.

14. The method of claim 10, wherein the nanogel has a hydrodynamic diameter ranging from 20 nm to 490 nm.

15. The method of claim 10, wherein the nanogel has a zeta potential ranging from −26.5 mV to −47.5 mV.

16. The method of claim 10, wherein the effective dose of the nanogel is at least 50 mg/kg of body weight of the subject.

17. The method of claim 10, wherein the subject is a mammal.

18. A method for preventing or treating metastasis in a subject in need thereof, comprising administering to the subject a pharmaceutical compositions comprising a nanogel, wherein the nanogel comprises a graphene-like nanosheet and a polysaccharide, and the graphene-like nanosheet comprises a carbonization product of at least a portion of the polysaccharide, and the graphene-like nanosheet is complexed with the polysaccharide to form a cross-linked supramolecular structure;

wherein the polysaccharide is a salt of alginic acid.

* * * * *